United States Patent
Courage et al.

(10) Patent No.: US 10,624,984 B2
(45) Date of Patent: *Apr. 21, 2020

(54) APTAMER-MODIFIED POLYMERIC MATERIALS FOR THE BINDING OF FACTORS IN A WOUND ENVIRONMENT

(71) Applicant: KCI Licensing, Inc., San Antonio, TX (US)

(72) Inventors: James Courage, San Antonio, TX (US); Diwi Allen, San Antonio, TX (US); Amy McNulty, San Antonio, TX (US); Anthony Rycerz, San Antonio, TX (US); Christopher Carroll, San Antonio, TX (US); Douglas Hanson, San Antonio, TX (US); Todd Fruchterman, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 105 days.

This patent is subject to a terminal disclaimer.

(21) Appl. No.: 15/172,552

(22) Filed: Jun. 3, 2016

(65) Prior Publication Data

US 2016/0346421 A1    Dec. 1, 2016

Related U.S. Application Data

(63) Continuation of application No. 13/458,071, filed on Apr. 27, 2012, now Pat. No. 9,382,290.

(60) Provisional application No. 61/518,148, filed on Apr. 29, 2011.

(51) Int. Cl.

| | |
|---|---|
| A61L 15/44 | (2006.01) |
| A61L 15/32 | (2006.01) |
| A61L 15/42 | (2006.01) |
| C07K 14/78 | (2006.01) |
| C07K 7/06 | (2006.01) |
| A61L 15/26 | (2006.01) |

(52) U.S. Cl.
CPC .............. *A61L 15/44* (2013.01); *A61L 15/26* (2013.01); *A61L 15/32* (2013.01); *A61L 15/425* (2013.01); *C07K 7/06* (2013.01); *C07K 14/78* (2013.01); *A61L 2300/414* (2013.01); *A61L 2300/426* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Kelling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

NCBI BLAST (Analysis for instant SEQ ID No. 1, downloaded from http://blast.ncbi.nlm.nih.gov/Blast.cgi on Feb. 2, 2013) (Year: 2013).*

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia StateUniversity, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

(Continued)

*Primary Examiner* — Brian Gangle
*Assistant Examiner* — Andrea K McCollum

(57) ABSTRACT

Aptamer-modified polymers and materials thereof, used for binding factors in a wound bed. The aptamer-modified materials can be polypeptides conjugated to polymer foam materials and used, for example, as dressings, wound inserts, or pads.

18 Claims, 18 Drawing Sheets

Specification includes a Sequence Listing.

(56) References Cited

U.S. PATENT DOCUMENTS

| | | | |
|---|---|---|---|
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,810,755 A | 9/1998 | LeVeen et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,555,645 B1 | 4/2003 | Ikeda et al. | |
| 6,814,079 B2 | 11/2004 | Heaton et al. | |
| 7,273,054 B2 | 9/2007 | Heaton et al. | |
| 7,777,091 B2 | 8/2010 | Park et al. | |
| 9,382,290 B2 * | 7/2016 | Courage | A61L 15/32 |
| 9,657,132 B2 * | 5/2017 | Hanson | C08G 18/40 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2007/0014837 A1 | 1/2007 | Johnson et al. | |
| 2008/0146983 A1 | 6/2008 | Park et al. | |
| 2008/0207535 A1 | 8/2008 | Urban et al. | |
| 2009/0075030 A1 | 3/2009 | Kokko et al. | |
| 2009/0093550 A1 | 4/2009 | Rolfes et al. | |
| 2009/0123516 A1 | 5/2009 | Agrawal et al. | |
| 2009/0177133 A1 | 7/2009 | Kieswetter et al. | |
| 2012/0156274 A1 | 6/2012 | Fugmann et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| WO | 80/02182 A1 | 10/1980 |
| WO | 87/04626 A1 | 8/1987 |
| WO | 9010424 A1 | 9/1990 |
| WO | 93/09727 A1 | 5/1993 |
| WO | 9420041 A1 | 9/1994 |
| WO | 96/05873 A1 | 2/1996 |
| WO | 97/18007 A1 | 5/1997 |
| WO | 99/13793 A1 | 3/1999 |
| WO | 2007103208 A2 | 9/2007 |
| WO | 2009/033088 A1 | 3/2009 |
| WO | 2010129547 A1 | 11/2010 |

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

(56) References Cited

OTHER PUBLICATIONS

Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Ohariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Amljots, Bjorn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. {hacek over (Z)}ivadinovic, V. uki , {hacek over (Z)}. Maksimovi , . Radak, and P. Pe{hacek over (s)}ka, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("SolovevGuidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29,1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. .RTM. Therapy Clinical Guidelines: A Reference Source for Clinicians (Jul. 2007).
Written Opinion for corresponding PCT application PCT/US2012/035343 dated Oct. 29, 2013.
Third Office Action regarding Chinese Application No. 201280013075.2 dated Jul. 19, 2016. Translation provided by AFD China Intellectual Property Law Office.
S Ikemoto et al.: "Laminin-peptide conjugated chitosan membrane: application for keratinocyte delivery in Wounded skin", Journal of Biomedical Materials Research.Part A,vol. 79A, No. 3, 2006, pp. 716-722,XP002680516,Wiley Periodicals Inc.ISSN: 1549-3296.
I Appleton: "Wound repair: the role of cytokines and vasoactive mediators", Journal of the Royal Society of Medicine., vol. 87, No. 9, Sep. 1, 1994 (Sep. 1, 1994), pp. 500-502, XP009079528, Royal Society of Medicine, London. ISSN: 0141-0768.
Extended European Search Report for corresponding Application No. 171904287, dated Dec. 19, 2017.

* cited by examiner

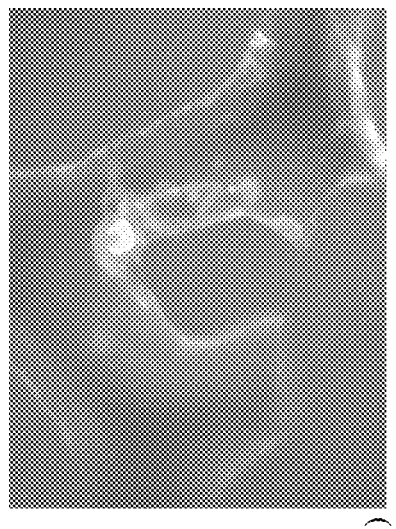
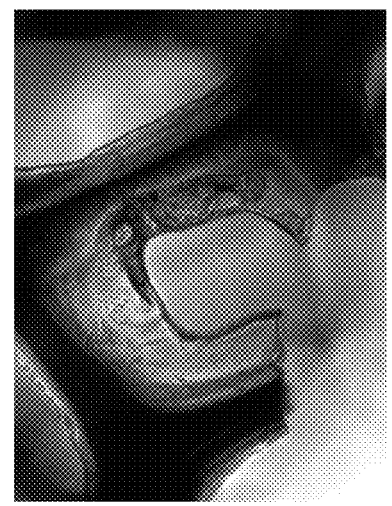
FIGS. 9A & B

SEQUENCE LISTING

```
<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: polypeptide

<400> SEQUENCE: 1

Asn Ala Ile Gln Glu Ala Arg Arg Leu Leu Asn Leu Ser Arg Asp
```

```
1               5               10              15

<210> SEQ ID NO 2
<211> LENGTH: 11
<212> TYPE: PRT
<213> ORGANISM: Artificial Sequence
<220> FEATURE:
<223> OTHER INFORMATION: oligopeptide

<400> SEQUENCE: 2

Gly His Gln Gly Gln His Ile Gly Gln Met Ser
1               5                   10

<210> SEQ ID NO 3
<211> LENGTH: 4
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (3)..(3)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 3

Ala Glu Glu Cys
1

<210> SEQ ID NO 4
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (14)..(14)
<223> OTHER INFORMATION: ACETYLATION
<220> FEATURE:
<221> NAME/KEY: MOD_RES
<222> LOCATION: (15)..(15)
<223> OTHER INFORMATION: AMIDATION

<400> SEQUENCE: 4

Gly His Gln Gly Gln His Ile Gly Gln Met Ser Ala Glu Glu Cys
1               5                   10                  15
```

APTAMER-MODIFIED POLYMERIC MATERIALS FOR THE BINDING OF FACTORS IN A WOUND ENVIRONMENT

The present application is a continuation of U.S. application Ser. No. 13/458,071 filed Apr. 27, 2012, which claims priority to U.S. Provisional Application Ser. No. 61/518,148 filed Apr. 29, 2011. The entire content of each of the above disclosures is incorporated herein by reference.

BACKGROUND

1. Field of the Invention

The present disclosure relates generally to healing of wounds and wound-treatment therapies. More particularly, but not by way of limitation, the present disclosure relates to modified materials, for example, silyl modified polyurethane foam for the reversible binding of factors in a wound bed.

2. Background Information

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. One of the major clinical benefits of negative pressure wound therapy is its ability to effectively eliminate wound exudate, thereby reducing edema and allowing tissue decompression. Negative pressure wound therapy may not always be able to differentiate between harmful and beneficial factors removed from the wound. Coating used to address this such as collagen, PVA, PEG, and fibrinogen often suffer from not being covalent, uniform, or target specific. Typically they cannot bind proteins at a specific site and present them to cells in a manner that allows the active site to retain its function. Improvements that would allow the binding of molecules in a covalent manner, specify the types of compounds that could be bound, the chemical reactions with which to bind them, and/or the orientation with which the protein is presented to the cells, e.g., for use in a dressing, wound insert, pad, etc., would therefore be highly desirable.

SUMMARY

The present disclosure provides novel materials, including aptamer (e.g., polypeptide) modified polymers, which may be used for the binding of factors, such as from a wound bed. In some embodiments, the factors are endogenous. In others they are exogenous. In some embodiments, the bind is reversible, in others it is irreversible.

In some embodiments a polypeptide is provided comprising an amino acid sequence identical to SEQ ID NO: 2 (P16; GHQGQHIGQMS), a sequence at least 90% identical to SEQ ID NO: 2 or a sequence comprising 1, 2, or 3 amino acid substitutions or deletions relative to SEQ ID NO: 2. In some aspects, the amino acid sequence further comprises an amino or carboxyl terminal Cys residue (e.g., the amino or carboxyl terminus of a polypeptide of the embodiments comprises a PEG spacer-cysteine residue). For example, the amino acid sequence can comprise the sequence AEEAc-Cys-NH$_2$ at the C-terminus. In still further aspects, a wound dressing is provided comprising a polymer foam substrate conjugated to a polypeptide of the embodiments, such as a polypeptide comprising an amino acid sequence of SEQ ID NO: 2 (GHQGQHIGQMS) or a sequence at least 90% identical to SEQ ID NO: 2.

In some embodiments, aptamer is an the oligopeptide having 8 to 12 residues. In some embodiments, the oligopeptide has the sequence GHQGQHIGQMS (SEQ ID NO: 2). In some embodiments, aptamer is P16. In some embodiments, aptamer is P22.

In some embodiments, a polypeptide of the embodiments is covalently attached to a polymer foam (e.g., to form a wound dressing). In some aspects, a polypeptide is attached to the polymer foam through a thioether linker. For example, the linker can be an EMCS-derived linker or a sulfo-EMCS-derived linker. In some aspects, the thioether linker comprises a Cys residue in the polypeptide, such as a Cys residue in a AEEAc-Cys-NH$_2$ sequence of the polypeptide. In still further aspects, a linker between a polypeptide and a polymer foam can be a silyl derived linker (e.g., a substituted silyl derived linker derived from aminoundecyltriethoxysilane or aminopropyldiisopropylethoxysilane). In still further aspects, a polypeptide of the embodiments is attached to a polymer foam via a non-covalent binding, such as by a biotin-avidin binding.

In certain aspects, a wound dressing of the embodiments further comprises a growth factor, chemokine or cytokine bound to the wound dressing (e.g., bound to the wound dressing via an interaction with a polypeptide of the embodiments). In some aspects, the growth factor is granulocyte macrophage colony stimulating factor (GM-CSF). In certain aspects, the growth factor is vascular endothelial growth factor (VEGF).

In some embodiments, a polypeptide of the embodiments is attached to a polymer foam to form a wound dressing. For example, the polymer foam substrate can be a reticulated open-celled foam. Examples of polymer foams include, without limitation, foam substrates comprising polyvinyl alcohol, polyurethane, polypropylene, polystyrene, polyols, poloxamer, aminoglycosides, amino sugars, or a combination of one or more of these.

In further embodiments a method is provided for binding a growth factor, chemokine or cytokine comprising contacting a fluid (such as a body fluid) comprising the growth factor, chemokine or cytokine with a wound dressing according to embodiments, thereby binding the growth factor, chemokine or cytokine. In some aspects, a wound dressing of the embodiments is adapted for using in applying negative pressure to a wound site. In further aspects, a method comprises removing some or all of the fluid in contact with the wound dressing. In still further aspects, a method of the embodiments further comprises contacting the wound dressing with at least a second fluid wherein some or all of the growth factor, chemokine or cytokine bound to the wound dressing is eluted into the second fluid. In certain aspects, a method of the embodiments is defined as an in vitro method.

In yet a further embodiment, a composition is provided for the treatment of a wound, comprising a wound dressing according to the embodiments. In some aspects, a method is provided for treating a wound comprising contacting a wound site with a wound dressing of the embodiments. In certain aspects, a method of the embodiments further comprises applying a negative pressure to the wound site.

Any embodiment of any of the present systems and/or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 9A & B provide images of silanated ROCF with Texas Red® fluorescent dye. FIG. 9A shows a Brightfield image showing the orientation and appearance of —Sil/ ROCF in regular light. FIG. 9B shows TRITC imaging of Texas Red® conjugated to 630 showing successful conjugation of the dye to the -Sil. This provides evidence that 630 was successfully deposited on the ROCF. Both images were taken at 20x magnification.

FIG. 17 depicts a schematic diagram according to some of the embodiments of the present invention. In this side view, an insert modified with specifically designed proteins is shown binding with different dissociation constants ($K_d$ values) to different factors. In this embodiment, the modified insert is being flushed (continuously or intermittently) with a treatment solution (metered bolus) containing a variety of agents, for example, agents for wound cleaning, promoting healing, solution stability, etc. The block arrow labeled "Exudate" represents mixture leaving the material, including treatment solution and exudate from a wound that dressing may be in contact with.

DESCRIPTION OF ILLUSTRATIVE EMBODIMENTS

Figure 1:
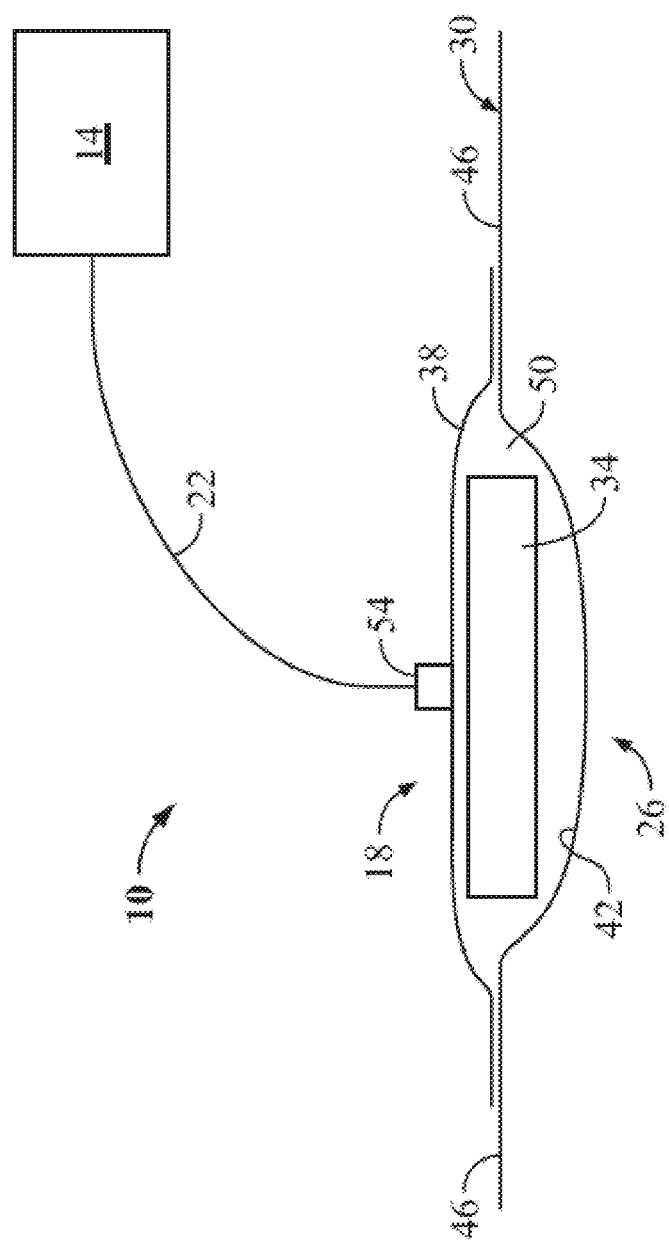
FIG. 1 depicts a side view of one embodiment of the present wound dressings having one of the present modified wound inserts and coupled to a wound site and to a wound treatment apparatus.

In some aspects, the present disclosure provides aptamer modified materials, which may be used, in some embodiments, as wound inserts for catching and concentrating specific factors in the wound environment, for example, factors triggering a biological response such as angiogenesis, or to deliver biomolecules or bioactive compounds to a wound bed. In some embodiments, the factors are endogenous. In others they are exogenous. In some embodiments the bind is reversible, in others it is irreversible.

In one aspect, the invention provides aptamer-functionalized wound dressings, comprising: (a) a substrate; and (b) an aptamer covalently attached to the polymer foam. In some embodiments, the substrate is a polymer foam. In some embodiments, the aptamer comprises a a polypeptide, a small-molecule binder, a dendrimer, a nanoparticle, and/or an oligonucleotide. In some embodiments, said aptamer is a polypeptide. In some embodiments, the polypeptide is synthetic. In some embodiments, the polypeptide is natural.

In some embodiments, the polypeptide is covalently attached to the polymer foam. In some embodiments, C-terminus of the polypeptide comprises a PEG spacer-cysteine residue. In some embodiments, the aptamer is attached to the polymer foam through a linker. In some embodiments, the linker is an EMCS-derived linker or a sulfo-EMCS-derived linker. In some embodiments, the linker is a substituted silyl derived linker. In some embodiments, the substituted silyl derived linker is derived from compound 630 (aminoundecyltriethoxysilane). In some embodiments, the substituted silyl derived linker is derived from compound 602 (aminopropyldiisopropylethoxysilane). In some embodiments, the linker comprises a first and second linker, wherein the first linker is an EMCS-derived linker or a sulfo-EMCS-derived linker and the second linker is a substituted silyl derived linker.

In some embodiments, the linker is bound to the polymer foam through an oxygen atom. In some embodiments, the linker is bound to the polymer foam through a nitrogen atom. In some embodiments, the aptamer is configured to bind to endogenous or exogenous factors in a wound environment. In some embodiments, the binding is irreversible. In some embodiments, the binding is reversible. In some embodiments, the aptamer is configured to bind to vascular endothelial growth factor. In some embodiments, the aptamer is configured to bind to platelet derived growth factor. In some embodiments, the aptamer is configured to bind to fibroblast growth factor. In some embodiments, the aptamer is configured to bind to keratinocyte growth factor. In some embodiments, the aptamer is configured to bind to granulocyte macrophage colony stimulating factor.

In some embodiments, the substrate is a reticulated open-celled foam. In some embodiments, the substrate comprises polyvinyl alcohol, polyurethane, polypropylene, polystyrene, polyols, poloxamer, aminoglycosides, amino sugars, or a combination of one or more of these. In some embodiments, the polymer foam comprises a first monomer subunit. In some embodiments, the first monomer subunit is a diisocyanate. In some embodiments, the diisocyanate is toluene diisocyanate, methylene diphenyl diisocyanate, or ethyl lysine diisocyanate. In some embodiments, the polymer foam further comprises a second monomer subunit. In some embodiments, the second monomer is a triol. In some embodiments, the triol is a PEGylated glycerine. In some embodiments, the polymer foam further comprises a third monomer subunit. In some embodiments, the third monomer subunit is an aminoglycoside. In some embodiments, the aminoglycoside is chitosan. In some embodiments, the aminoglycoside is glucosamine. In some embodiments, the third monomer subunit is neomycin. In some embodiments, the third monomer subunit is dibekacin. In some embodiments, the third monomer subunit is kanamycin. In some embodiments, the third monomer subunit is tobramycin. In some embodiments, the third monomer subunit is streptomycin. In some embodiments, the third monomer subunit is gentamicin. In some embodiments, the polymer foam further comprises an oligomeric subunit. In some embodiments, the oligomeric subunit is a chitosan-based oligomer. In some embodiments, the oligomeric subunit is a glucosamine-based oligomer.

In another aspect, the invention provides aptamer-modified polymers, wherein the polymer backbone comprises a first repeat unit of the formula:

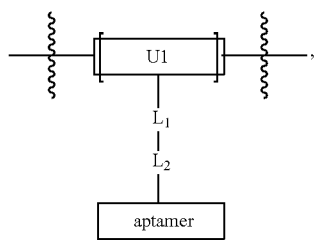

wherein:
U1 is the unmodified portion of the first repeat unit;
L₁ is a linker molecule or a bond; and
L₂ is a linker molecule or a bond.

In some embodiments, L1 is a bond and the formula of the first repeat unit is further defined as:

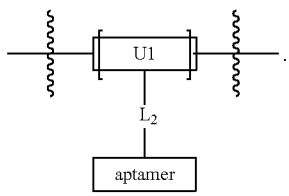

In some embodiments, L2 is a bond and the formula of the first repeat unit is further defined as:

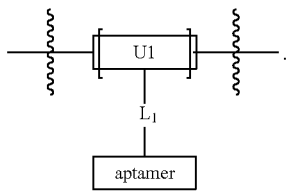

In some embodiments, L1 and L2 are bonds and the formula of the first repeat unit is further defined as:

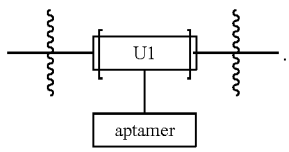

In some embodiments, U1 is of the formula:

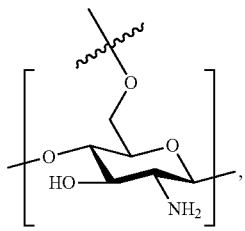

wherein the point of attachment of the side chain connects to $L_1$.

In some embodiments, U1 is of the formula:

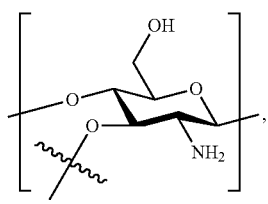

wherein the point of attachment of the side chain connects to $L_1$.

In some embodiments, U1 is of the formula:

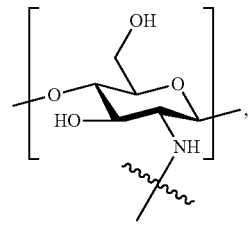

wherein the point of attachment of the side chain connects to L1.

In some embodiments, U1 is of the formula:

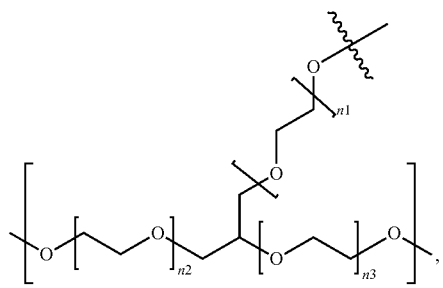

wherein:
n1, n2 and n3 are each independently from 0 to 20; and
the point of attachment of the side chain connects to $L_1$.

In some embodiments, U1 is based on a triol-based monomer. In some embodiments, the triol-based monomer is a PEGylated glycerine molecule having a molecular weight between 500 and 5,000 g/mole.

In some embodiments, $L_1$ is of the formula $—O—Si(R_1)(R_2)—R_3—X—$, wherein:
$R_1$ and $R_2$ are independently hydrogen, hydroxy, halo, alkyl$_{(C≤6)}$ or alkoxy$_{(C≤6)}$;
$R_3$ is alkanediyl$_{(C≤6)}$; and
X is —NH—, —C(O)— or —S—; and wherein X is connected to $L_2$ or to the aptamer.

In some embodiments, $R_1$ and $R_2$ are isopropyl. In some embodiments, $R_1$ and $R_2$ are hydroxy. In some embodiments, $R_3$ is alkanediyl$_{(C3-11)}$. In some embodiments, $R_3$ is —(CH$_2$)$_3$—. In some embodiments, $R_3$ is —(CH$_2$)$_{11}$—. In some embodiments, X is —NH—.

In some embodiments, $L_1$ or $L_2$ is an amino thio linker. In some embodiments, $L_1$ or $L_2$ is an NHS-Maleimide crosslinker. In some embodiments, $L_1$ or $L_2$ is an NHS-Haloacetyl crosslinker. In some embodiments, $L_1$ or $L_2$ is an NHS-Pyridyldithiol crosslinker.

In some embodiments, the amino thio linker is derived from a reagent selected from the group consisting of SM(PEG)24, SM(PEG)12, SM(PEG)8, SM(PEG)6, SM(PEG)4, Sulfo-LC-SMPT, SM(PEG)2, Sulfo-KMUS, LC-SMCC, LC-SPDP, Sulfo-LC-SPDP, SMPH, Sulfo-SMPB, SMPB, SMPT, STAB, Sulfo-SIAB, Sulfo-EMCS, EMCS, Sulfo-SMCC, SMCC, MBS, GMBS, Sulfo-GMBS, Sulfo-MBS, SPDP, SBAP, BMPS, AMAS, and SIA.

In some embodiments, the aptamer-modified polymer comprises a second repeat unit. In some embodiments, the second repeat unit is a chitosan-based oligomer.

In some embodiments, U1 is of the formula:

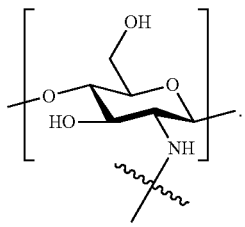

wherein the point of attachment of the side chain connects to L1.

In some embodiments, L1 is of the formula:

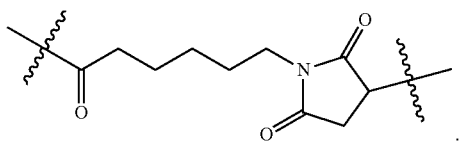 [SMILES: *C(=O)CCCCCN1C(=O)CC(*)C1=O]

In some embodiments, L2 is of the formula:

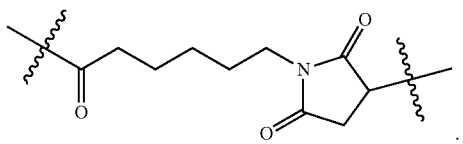 [SMILES: *C(=O)CCCCCN1C(=O)CC(*)C1=O]

In some embodiments, L2 is of the formula —C(O)(CH2)5-S-Cys-AEEAc—, wherein AEEAc is:

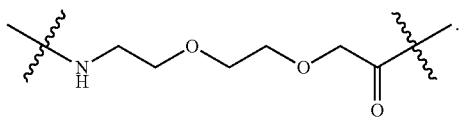 [SMILES: *NCCOCCOCC(*)=O]

In some embodiments, the aptamer-modified polymer further comprises a second repeat unit.

In some embodiments, the second repeat unit has the formula:

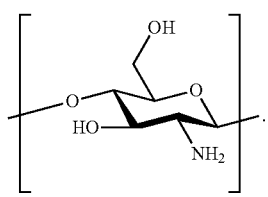

In some embodiments, aptamer is an the oligopeptide having 8 to 12 residues. In some embodiments, the oligopeptide has the sequence GHQGQHIGQMS. In some embodiments, aptamer is P16. In some embodiments, aptamer is P22.

In some embodiments, the aptamer-modified polymer further comprises a third repeat unit of the formula:

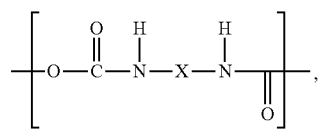

wherein X is:
alkanediyl$_{(C≤12)}$⁻;
arenediyl$_{(≤12)}$⁻;
arenediyl$_{(≤6)}$—CH$_2$-arenediyl$_{(≤6)}$; or
substituted versions of any these groups.

In some embodiments, X is further defined as:

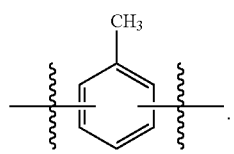

In some embodiments, the third repeat unit is a polyurethane repeat unit. In some embodiments, the third repeat unit is an ether-based polyurethane repeat unit. In some embodiments, the third repeat unit is an ester-based polyurethane repeat unit. In some embodiments, the polymer is an open-celled foam.

In another aspect, the invention provides an aptamer-modified polymer or co-polymer comprising:
a) a first repeat unit having one or more hydroxy groups;
b) a second repeat using having one or more —O—Si(R$_1$)(R$_2$)—R$_3$—X-linker-aptamer groups, wherein:
R$_1$ and R$_2$ are independently hydrogen, hydroxy, halo, alkyl$_{(C≤6)}$ or alkoxy$_{(C≤6)}$;
R$_3$ is alkanediyl$_{(C≤20)}$;
X is —NH— or —S—;
the linker is —C(O)-alkanediyl$_{(C≤12)}$⁻; and
the aptamer is a biologically active protein that is bound to the linker group through either an amino, a hydroxy or a mercapto group.

In some embodiments, the first repeat unit has two hydroxy groups.

In some embodiments, the first repeat unit has the formula:

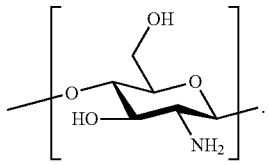

In some embodiments, R$_1$ and R$_2$ are isopropyl. In some embodiments, wherein R$_1$ and R$_2$ are hydroxy. In some embodiments, R$_3$ is alkanediyl$_{(C3-11)}$. In some embodiments, R$_3$ is —(CH$_2$)$_3$—.

In some embodiments, the second repeat unit has the formula:

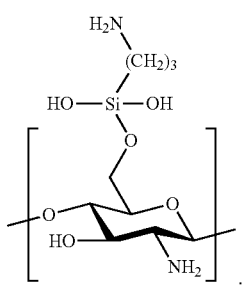

In some embodiments, $R_3$ is —$(CH_2)_{11}$—. In some embodiments, the second repeat unit has the formula:

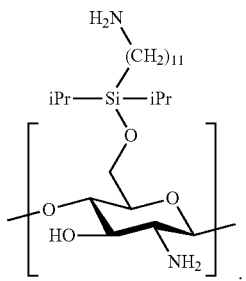

In some embodiments, X is —NH—. In some embodiments, the linker is further defined by the formula:

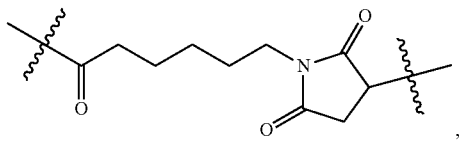 [SMILES: *C(=O)CCCCCN1C(=O)CC(*)C1=O]

wherein the carbonyl carbon is attached to X.

In some embodiments, the aptamer is bound through the linker through the mercapto group of a cysteine residue. In some embodiments, the aptamer is granulocyte-macrophage colony stimulating factor (GM-CSF).

In some embodiments, the aptamer-modified polymer further comprises a third repeat unit of the formula:

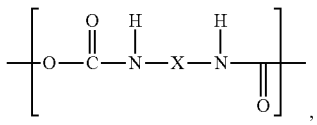

wherein X is:

alkanediyl$_{(C≤12)}$—;

arenediyl$_{(≤12)}$—;

arenediyl$_{(≤6)}$—CH$_2$-arenediyl$_{(≤6)}$—; or substituted versions of any these groups.

In some embodiments, X is further defined as:

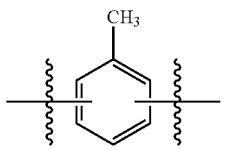

In some embodiments, the third repeat unit is a polyurethane repeat unit. In some embodiments, the third repeat unit is an ether-based polyurethane repeat unit. In some embodiments, the third repeat unit is an ester-based polyurethane repeat unit. In some embodiments, the polymer is an open-celled foam.

In another aspect, the invention provides a wound insert comprising an aptamer-modified polymer or co-polymer as described above or below. In another aspect, the invention provides a wound dressing comprising the wound insert and a drape configured to be coupled to skin adjacent a wound of a patient. In some embodiments, the wound dressing further comprises a fluid delivery pad configured to be coupled to the drape and a fluid source such that the fluid source is actuatable to deliver a fluid to a wound through the wound dressing.

In another aspect, the invention provides a wound-treatment apparatus comprising the wound dressing and a fluid source configured to be coupled to the wound dressing such that the fluid source is actuatable to deliver a fluid to the wound dressing. In some embodiments, the apparatus further comprising a vacuum source configured to be coupled to the wound dressing such that the vacuum source is actuatable to apply negative pressure to the wound dressing. In some embodiments, the fluid comprises a functional solution that enhances target binding or facilitates target release into the wound bed. In some embodiments, the fluid comprises saline solutions, solutions with slightly acidic pH, slightly basic pH, solutions with various surfactants (e.g., polysorbate), EDTA and/or EGTA. In some embodiments, the fluid comprises hypochlorous acid and hypochlorite ion.

A. DEFINITIONS

As used herein, the term "aptamer" refers not only to oligonucleic acid or peptide molecules that bind to a specific target molecule, but also to any ligand that binds to a target molecule or ion. For example, as used herein, "aptamer" would include EDTA (ethylene-diaminetetraacetic acid), which binds to $Ca^{2+}$.

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means=NH (see below for definitions of groups containing the term imino, e.g., alkylimino); "cyano" means —CN; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means=S; "thioether" means —S—; "sulfonamido" means —NHS(O)$_2$—(see below for definitions of groups containing the term sulfonamido, e.g., alkylsulfonamido); "sulfonyl" means —S(O)$_2$—(see below for definitions of groups containing the term sulfonyl, e.g., alkylsulfonyl); and "sulfinyl" means —S(O)—(see below for definitions of groups containing the term sulfinyl, e.g., alkylsulfinyl).

The symbol "—" means a single bond, "=" means a double bond, and "≡" means triple bond. The symbol "---" represents an optional bond, which if present is either single or double. The symbol "=" represents a single bond or a double bond. Thus, for example, the structure

includes the structures

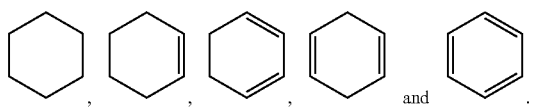 and .

As will be understood by a person of skill in the art, no one such ring atom forms part of more than one double bond. The symbol "~", when drawn perpendicularly across a bond indicates a point of attachment of the group. It is noted that the point of attachment is typically only identified in this manner for larger groups in order to assist the reader in rapidly and unambiguously identifying a point of attachment. The symbol "◄" means a single bond where the group attached to the thick end of the wedge is "out of the page." The symbol "⬛" means a single bond where the group attached to the thick end of the wedge is "into the page". The symbol "~" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

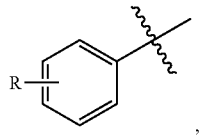

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

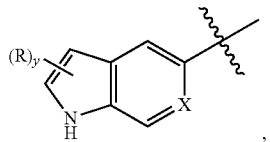

then R may replace any hydrogen attached to any of the ring atoms of either of the fused rings unless specified otherwise.

Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups, —CH=CHF, —CH=CHCl and —CH=CHBr, are non-limiting examples of substituted alkenyl groups. An "alkene" refers to the compound H—R, wherein R is alkenyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

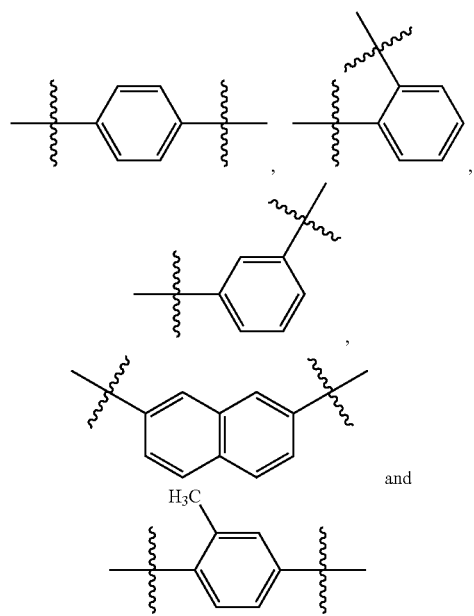

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the group consists of no atoms other than carbon, hydrogen, aromatic nitrogen, aromatic oxygen and aromatic sulfur. As used herein, the term does not preclude the presence of one or more alkyl group (carbon number limitation permitting) attached to the aromatic ring or any additional aromatic ring present. Non-limiting examples of heteroaryl groups include furanyl, imidazolyl, indolyl, indazolyl (Im), methylpyridyl, oxazolyl, pyridyl, pyrrolyl, pyrimidyl, pyrazinyl, quinolyl, quinazolyl, quinoxalinyl, thienyl, and triazinyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of heteroarenediyl groups include:

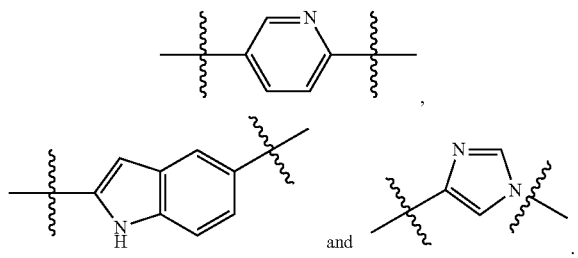

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. Similarly, the term "alkylthio" when used without the "substituted" modifier refers to the group —SR, in which R is an alkyl, as that term is defined above. The term "alkoxydiyl" when used without the "substituted" modifier refers to the divalent group —O-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "glycoside" refers to a compound in which a sugar group is bound to a non-carbohydrate moiety. Typically the sugar group (glycone) is bonded through its anomeric carbon to another group (aglycone) via a glycosidic bond that has an oxygen, nitrogen or sulfur atom as a linker.

A "simple sugar" are the basic structural units of carbohydrates, which cannot be readily hydrolyzed into simpler units. The elementary formula of a simple monosaccharide is $C_nH_{2n}O_n$, where the integer n is at least 3 and rarely greater than 7. simple monosachharides may be named generically according on the number of carbon atoms n: trioses, tetroses, pentoses, hexoses, etc. Simple sugars may be open chain (acyclic), cyclic or mixtures thereof. In these cyclic forms, the ring usually has 5 or 6 atoms. These forms are called furanoses and pyranoses, respectively—by analogy with furan and pyran. Simple sugars may be further classified into aldoses, those with a carbonyl group at the end of the chain in the acyclic form, and ketoses, those in which the carbonyl group is not at the end of the chain. Non-limiting examples of aldoses include: glycolaldehyde, glyceraldehydes, erythrose, threose, ribose, arabinose, xylose, lyxose, allose, altrose, glucose, mannose, gulose, idose, galactose and talose. Non-limiting examples of aldoses include: dihydroxyacetone, erythrulose, ribulose, xylulose, fructose, psicose, sorbose and tagatose. The 'D-' and 'L-' prefixes may be used to distinguish two particular stereoisomers which are mirror-images of each other. The term simple sugar also covers O-acetyl derivatives thereof.

An "amino sugar" or "aminoglycoside" refers to a derivative of a sugar, deoxy sugar, sugar acid or sugar alcohol, where one or more hydroxy group(s) has been replace with one more amino group(s). A "simple amino sugar" refers to a derivative of a simple sugar, simply deoxy sugar, simply sugar acid or sugar alcohol, where one or more hydroxy group(s) has been replace with one more amino group(s). These terms also cover N- and O-acetyl derivatives thereof. Non-limiting examples include N-acetylglucosamine, galactosamine, glucosamine and sialic acid.

The term "deoxy sugar" refers to a sugar derivative where one of the hydroxy groups of a carbohydrate has been replaced with a hydrogen atom. A "simple deoxy sugar" is a deoxy sugar derived from a simple sugar, as defined herein. These terms also cover O-acetyl derivatives thereof. Non-limiting examples of simple deoxy sugars are deoxyribose (based upon ribose), fucose, and rhamnose.

The term "sugar acid" refers to a sugar derivative where an aldehyde functional group or one or more hydroxy functional groups has been oxidized to a carboxyl group. Aldonic acids are those in which the aldehyde functional group of an aldose has been oxidized. Ulosonic acids are those in which the first hydroxyl group of a 2-ketose has been oxidized creating an t-ketoacid. Uronic acids are those in which the terminal hydroxyl group of an aldose or ketose has been oxidized. Aldaric acids are those in which both ends of an aldose have been oxidized. Non-limiting aldonic acids include glyceric acid (3C), xylonic acid (5C), gluconic acid (6C), and ascorbic acid (6C, unsaturated lactone). Non-limiting examples of ulosonic acids include neuraminic acid (5-amino-3,5-dideoxy-D -glycero-D-galacto-non-2-ulosonic acid) and ketodeoxyoctulosonic acid (KDO or 3-deoxy-D-manno-oct-2-ulosonic acid). Non-limiting examples of uronic acids include glucuronic acid (6C), galacturonic acid (6C), and iduronic acid (6C). Non-limiting example of aldaric acids include tartaric acid (4C), meso-galactaric acid (mucic acid) (6C), and D-glucaric acid (saccharic acid) (6C). A "simple sugar acid" is a sugar acid derived from a simple sugar. These terms also cover O-acetyl derivatives thereof.

The term "sugar alcohol" refers to a sugar derivative whose carbonyl group (aldehyde or ketone, reducing sugar) has been reduced to a primary or secondary hydroxyl group. Non-limiting examples of sugar alcohols include: glycol (2-carbon), glycerol (3-carbon), erythritol (4-carbon), threitol (4-carbon), arabitol (5-carbon), xylitol (5-carbon), ribitol (5-carbon), mannitol (6-carbon), sorbitol (6-carbon), dulcitol (6-carbon), iditol (6-carbon), isomalt (12-carbon), maltitol (12-carbon), lactitol (12-carbon) or polyglycitol. A "simple sugar alcohol" is a sugar alcohol derived from a simple sugar. These terms also cover O-acetyl derivatives thereof.

As used herein, the term "monosaccharide group" refers to a monovalent carbohydrate group, with a carbon atom as the point of attachment. The term covers the groups resulting from removal of a hydroxyl radical from a simple sugar (e.g., glucose), simple deoxy sugar (e.g., fucose), simple sugar acid (e.g., gluconic acid), simple sugar alcohol (e.g., xylitol) or simple amino sugar (e.g., glucosamine). Typically the monosaccharide group is bonded through its anomeric carbon to another group (aglycone) via oxygen atom linker. In some cases the linker may be a nitrogen or sulfur atom.

A "disaccharide group" is a monovalent carbohydrate group consisting of two monosaccharide groups, wherein the second monosaccharide group replaces a hydrogen on a hydroxy group of the first monosaccharide group. Non-limiting examples of disaccharide groups include those derived from sucrose, lactulose, lactose, maltose trehalose and cellobiose.

A "trisaccharide group" is a monovalent carbohydrate group consisting of three monosaccharide groups, wherein the second monosaccharide group replaces a hydrogen on a hydroxy group of the first monosaccharide group and the third monosaccharide group replaces a hydrogen on a hydroxy group of either the first or the second monosaccharide groups.

An oligosaccharide is a monovalent carbohydrate group consisting of three to ten, preferably three to six monosaccharide groups, wherein the second monosaccharide replaces a hydrogen on a hydroxy group of the first monosaccharide, the third monosaccharide replaces a hydrogen on a hydroxy group of either the first or the second monosaccharide groups, and subsequent monosaccharide groups replace hydrogens on any previously joined monosaccharide groups, thus forming either a linear or branched structure.

The term "silyl" when used without the "substituted" modifier refers to the group —SiR$_3$, where each R is independently hydrogen or unsubstituted alkyl, as that group is defined above. The term "substituted silyl" refers to the group, —SiR$_3$, wherein at least one of the R groups and as many as all of the R groups, is independently a substituted alkyl or —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. Any remaining R groups of the substituted silyl group are independently hydrogen or unsubstituted alkyl. The term "silylated" or "silanated" indicates that a given compound has been derivatized to contain a silyl and/or substituted silyl group. The abbreviation "—Sil" refers to silyl and/or substituted silyl groups.

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a wound dressing that "comprises," "has," "includes" or "contains" one or more elements possesses those one or more elements, but is not limited to possessing only those elements. For example, in a wound dressing that comprises a wound insert and a drape, the wound dressing includes the specified elements but is not limited to having only those elements. For example, such a wound dressing could also include a connection pad configured to be coupled to a wound-treatment apparatus.

The term "effective," as that term is used in the specification and/or claims, means adequate to accomplish a desired, expected, or intended result.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"PBS" is phosphate buffered saline; "phr" is parts per hundred resin; "OPA" is ortho-pthaldialdehyde; "RT" is room temperature.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis (3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts:Properties, and Use* (P. H. Stahl & C. G. Wermuth eds., Verlag Helvetica Chimica Acta, 2002).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "polymer" includes "copolymers."

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[$CH_2CH_2$]$_n$—, the repeat unit is —$CH_2CH_2$—. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc.

The term "reticulated open cell foam" or ROCF refers to a foam material with a porous structure consisting of an interconnected network of solid struts. The open cells are formed by the reticulation process, which is in turn defined as in the form of a network or having a network of parts. Because all struts are connected, the open cell porosity is also connected creating a continuously porous material. The ROCF can be defined specifically by three independent properties; pore size, relative density, and base material. In some embodiments, ROCF is made from polyurethane.

| | |
|---|---|
| GM-CSF | Granulocyte Macrophage Colony Stimulating Factor |
| P22 | Commercially available anti-GM-CSF Peptide |
| ROCF | Reticulated open cell foam |
| VEGF | Vascular endothelial growth factor |
| P16 | Anti-VEGF peptide designed de novo |
| 602 | Gelest Compound SIA0602.0, a monoethoxysilane |
| 630 | Gelest Compound SIA0630.0, a triethoxysilane |
| RFUs | Relative Fluorescent Units |
| TRITC | Tetramethylrhodamine isothiocyanate, commonly used for fluorescent microscopy |
| Sulfo-EMCS | ([N-e-Maleimidocaproyloxy] sulfosuccinimide ester) |
| NHS ester | N-hydroxysuccinimide ester |
| EtOH | Ethanol |
| Ex/Em | Excitation/Emission |
| OPA | Ortho-pthaldialdehyde |
| DI $H_2O$ | Deionized water |
| RT | Room Temperature |
| aa | Amino acid |
| ELISA | Enzyme-linked immunosorbent assay |
| EtOH | Ethanol |

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

Further, a device or structure that is configured in a certain way is configured in at least that way, but it can also be configured in other ways than those specifically described.

B. APTAMER MODIFIED MATERIALS

In one aspect the present invention provides a covalent system for catching and concentrating specific factors in the wound environment, including factors that trigger a significant biological response, such as proliferation, differentiation, or angiogenesis. This technology may be used, for example, to deliver biomolecules or bioactive compounds to the wound bed. Aptamer modified materials provided herein may be used in some embodiments as a system for catching and concentrating specific factors in the wound environment, for example, factors triggering a biological response such as angiogenesis, or to deliver endogenous or exogenous biomolecules or bioactive compounds to the wound bed.

In one aspect, the aptamer modified materials are provided comprising at least three components: (1) a polymer, (2) at least one linker covalently attached to the polymer, e.g., directly, through a side chain of the polymer, or through another linker molecule connected to the polymer, and (3) at least one aptamer molecule, which may be covalently attached to the polymer backbone, but will be more typically covalently attached to a linker.

1) Suitable Polymers

Polymers for use with the present invention include hydrophobic or hydrophilic polyurethanes, chitosan, crosslinked and/or uncrosslinked polyolefins, polyols, ethylene vinyl acetate (EVA), elastomers such as acrylonitrile butadiene (NBR), polychloroprene (PCP or CR), ethylene propylene rubber (EPR & EPDM), poloxamers, silicones, and/or fluoro carbon polymers. For example, in some embodiments, a chitosan-based polyurethane polymer may be used.

Polyurethanes are reaction polymers. A urethane linkage is produced by reacting an isocyanate group, —N=C=O with a hydroxy group, and polyurethanes are produced by the polyaddition reaction of a polyisocyanate with a diol or a polyol, typically in the presence of a catalyst and other additives. A polyisocyanate is a molecule with two or more isocyanate functional groups, R—(N=C=O)$_n$, wherein n≥2 and a polyol is a molecule with two or more hydroxyl functional groups, R'—(OH)$_n$, wherein ≥2. The reaction product is a polymer containing the urethane linkage, —RNHCOOR'—. Polyurethanes may be produced by reacting a liquid isocyanate with a liquid blend of polyols, catalyst, and other additives. The blend of polyols and other additives may also be called a resin or a resin blend. In some embodiments, resin blend additives may include chain extenders, cross linkers, surfactants, flame retardants, blowing agents, pigments, and/or fillers. The synthesis of breathable or air-permeable, open cell, flexible urethane polymers is taught for example by U.S. Pat. No. 5,686,501, which is incorporated by reference herein in its entirety.

Molecules that contain two isocyanate groups are called diisocyanates. Isocyanates may be classed as aromatic, such as diphenylmethane diisocyanate (MDI), diphenylethane diisocyanate (EDI), or toluene diisocyanate (TDI); or aliphatic, such as hexamethylene diisocyanate (HDI) or isophorone diisocyanate (IPDI). An example of a polymeric isocyanate is polymeric diphenylmethane diisocyanate, which is a blend of molecules with two-, three-, and four- or more isocyanate groups. Isocyanates can be further modified by partially reacting them with a polyol to form a prepolymer. A "quasi-prepolymer" is formed when the stoichiometric ratio of isocyanate to hydroxyl groups is greater than 2:1. A "true prepolymer" is formed when the stoichiometric ratio is equal to 2:1. Important characteristics of isocyanates include their molecular backbone, % NCO content, functionality, and viscosity.

Molecules that contain two hydroxyl groups are called diols. Examples include, ethylene glycol (EG), 1,4-butanediol (BDO), diethylene glycol (DEG). Molecules that contain three hydroxyl groups are called triols. Examples include glycerol. Polyols may themselves be polymers. For example, they may be formed by base-catalyzed addition of propylene oxide (PO), ethylene oxide (EO) onto a hydroxy or amino-containing initiator, or by polyesterification of a di-acid, such as adipic acid, with glycols, such as ethylene glycol or dipropylene glycol (DPG). Polyols extended with PO or EO are typically called polyether polyols. Polyols formed by polyesterification are typically called polyester polyols. The choice of initiator, extender, and molecular weight of the polyol will typically affect its physical state, and the physical properties of the resulting polyurethane. Important characteristics of polyols are their molecular backbone, initiator, molecular weight, % primary hydroxyl groups, functionality, and viscosity.

One attribute of polyurethanes is its ability to be turned into foam. Small amounts of water may also be added to accomplish this in some embodiments. Water will react with isocyanate to create carbon dioxide gas, which fills and expands cells created during the mixing process. Blowing agents may also be used, including certain halocarbons such as HFC-245fa (1,1,1,3,3-pentafluoropropane) and HFC-134a (1,1,1,2-tetrafluoroethane), and hydrocarbons such as n-pentane. In some embodiments, surfactants may be used to modify the characteristics of the polymer during the foaming process.

Though the properties of the polyurethane are typically determined mainly by the choice of polyol, the diisocyanate exerts some influence. For example, the cure rate will generally be influenced by the reactivity of a given functional group and the number of functional isocyanate groups.

Softer, elastic, and more flexible polyurethanes typically result when linear difunctional polyethylene glycol segments, commonly called polyether polyols, are used to create the urethane links. More rigid products typically result if polyfunctional polyols are used, as these create a three-dimensional cross-linked structure which, again, can be in the form of a low-density foam. Control of viscoelastic properties, for example, by modifying the catalysts and polyols used can lead to memory foam, which is much softer at skin temperature than at room temperature.

In some embodiments of the present invention, the polyurethane foam is formed by the polymerization of isocyanates and polyols, typically toluene diisocyanate and a multi arm polyether polyol. These components may be indexed, such that the isocyanate and hydroxyl group are in a one to one ratio.

Chitosan is a linear polysaccharide derived from the exoskeletons of crustaceans, which can be represented in some embodiments by the following formula:

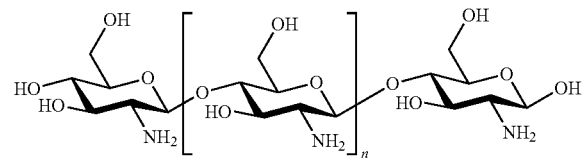

In some embodiments, chitosan is a linear polysaccharide composed of randomly distributed β-(1-4)-linked D-glucosamine (deacetylated unit) and N-acetyl-D-glucosamine (acetylated unit). The presence of the hydroxy groups and amino groups allows the utilization of a wide variety of conjugation chemistries. For example, chitosan may be polymerized and/or co-polymerized with diisocyanate or triisocyanate molecules, including diisocyanate or triisocyanate prepolymers, into a polyurethane polymer or co-polymer.

Figure 7:
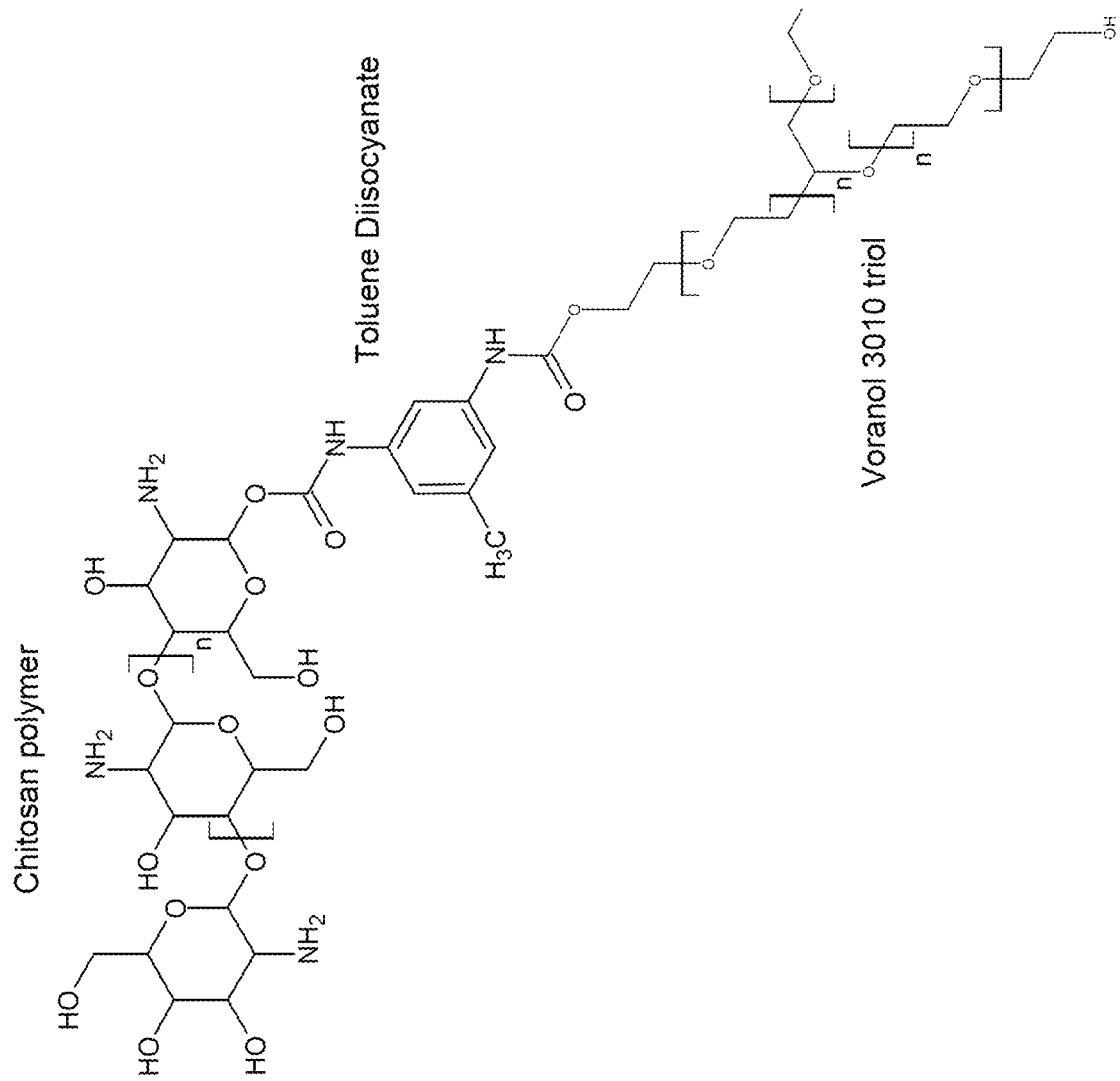
FIG. 7 depicts three repeat units of a polyurethane based on the polymerization of toluene diisocyanate (TDI), chitosan, and Voranol™ 3010 triol.

In some embodiments a polyol other than chitosan may be used in addition to the chitosan. Addition of chitosan to a polyol resin creates urethane bonds between the isocyanate and the hydroxyl groups on the chitosan ring. The resulting foam contains chitosan segments to be available on the struts of the foam and gives the foam some of the properties of chitosan. In addition the addition of chitosan produces an over-indexed foam, with surplus hydroxyl groups and amine groups on the chitosan segments that are available for additional surface chemistry. For example, FIG. 7 depicts a repeat units of polyurethane based on the polymerization of TDI, chitosan, and Voranol™ 3010 triol. In some embodiments chitosan or another diol or polyol may be polymerized into polyurethane at a ratio of 0.05-0.5 g chitosan per 1.0 g of a diisocyanate molecule or prepolymer. Further details and examples of such procedures are provided in the Examples section below.

Formulations of 5, 10, 20 and 30 PHR (grams of chitosan Per Hundred grams of polyurethane Resin) have been produced and tested. They have been characterized by the amount of surface amine available for bonding by conjugation of the foam with o-phthaldialdehyde. The relative fluorescence units RFU were found to be proportional to the primary amine available on the surface of the foam.

2) Linker-Modified Polymer Backbone

In some embodiments, the invention provides substituted silyl-modified polymers. Examples include those comprising repeat units based on polyurethane, which may be hydrophobic or hydrophilic, chitosan, crosslinked and/or uncrosslinked polyolefin, polyols, ethylene vinyl acetate (EVA), elastomers such as acrylonitrile butadiene (NBR), polychloroprene (PCP or CR), ethylene propylene rubber (EPR & EPDM), silicones, and/or fluoro carbon polymers. For example, in some embodiments, a chitosan-based polyurethane polymers or copolymers may be used. In some embodiments, the substituted silyl groups are attached to the polymer or co-polymer through an oxygen atom. In other embodiments, the substituted silyl groups are attached directly to a carbon atom of the polymer or co-polymer.

In some embodiments, the present invention provides polymeric materials modified with substituted silyl groups, for example, $(H_2N(CH_2)_3)(i\text{-}Pr)_2Si$— and $(H_2N(CH_2)_{11})(EtO)_2Si$—. In some embodiments, the materials of the present invention comprise a polymeric foam. Examples of foam materials can include polyurethane-based foam, which may be hydrophobic or hydrophilic, including, for example a chitosan-based polyurethane foam material. Other foams that may be suitable include chitosan, crosslinked and/or uncrosslinked polyolefin's, polyols, ethylene vinyl acetate (EVA), and elastomers such as acrylonitrile butadiene (NBR), polychloroprene (PCP or CR), ethylene propylene rubber (EPR & EPDM), silicones, and fluoro carbon polymers. For example, in some embodiments, a chitosan-based polyurethane foam may be used. In some embodiments, the substituted silyl groups are attached to the foam through an oxygen atom. In other embodiments, the substituted silyl groups are attached directly to a carbon atom of the foam.

The silylated polyurethane foams disclosed herein may be made by silylating the hydroxy groups on a polymer comprising such groups. As used herein, silylation is the introduction of a substituted silyl group ($R_3Si$—) to a molecule. It involves the replacement of a hydrogen on the compound, e.g., the hydrogen of a hydroxy group, with an substituted silyl group, for example, the compound 3-aminopropyldiisopropylethoxysilane will react with hydroxy groups under the appropriate conditions such groups to form a new covalent Si—O bond thereby linking the $H_2N(CH_2)_3Si(iPr)_2$— group to an oxygen which is in turn attached to the point of attachment on the molecule where the hydroxy group had been previously attached. Without being bound be mechanism, the oxygen atom of the product, may be the same oxygen atom of the hydroxy group reactant. See "How do I apply my Silane?" Gelest Catalog. 2006, pages 19-20, which are incorporated by reference herein in their entirety.

Example 1 below describes in detail how amino-substituted silyl groups may be deposited on 30 PHR chitosan foam. Example 2, describes how maleimide-thiol conjugation can be performed with Sulfo-EMCS, which has the formula:

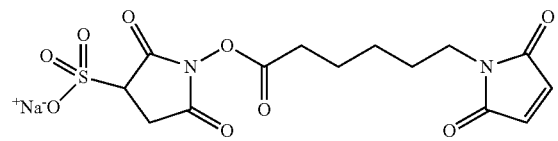

In some embodiments, the N-hydroxysuccinimide ester (NHS ester) on one end of the Sulfo-EMCS molecule can react with free amino groups of the linker or polymer. The maleimide group on the other end of the molecule may be used to react, for example, with —SH groups on a peptide aptamer to form stable thioether bonds. In this manner the Sulfo-EMCS may be used to link the peptide to a polymer or copolymer, including a foam substrate.

Furthermore, the peptides used in maleimide-thiol conjugation typically have specially modified C-termini. For example, the C-termini may be "capped" with Cys residues bearing reactive —SH groups to facilitate the conjugation. In a Sulfo-EMCS conjugations, Sulfo-EMCS is typically used in excess, for example, in 50-100× molar excess relative to an organosilane crosslinkers to facilitate the reaction. Such reactions may be carried out, for example, at pH 7.0-7.5 and at room temperature. Such methods may be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is also incorporated by reference herein in its entirety. For example, other suitable amino-thio linkers may be used. These include, for example: SM(PEG)24, SM(PEG)12, SM(PEG) 8, SM(PEG)6, SM(PEG)4, Sulfo-LC-SMPT, SM(PEG)2, Sulfo-KMUS, LC-SMCC, LC-SPDP, Sulfo-LC-SPDP, SMPH, Sulfo-SMPB, SMPB, SMPT, SIAB, Sulfo-SIAB, EMCS, Sulfo-SMCC, SMCC, MBS, GMBS, Sulfo-GMBS, Sulfo-MBS, SPDP, SBAP, BMPS, AMAS, and SIA.

In some embodiments of the present invention, the silylated polymer will be further modified with additional linker molecules, for example, oligopeptide oligomers. In some embodiments, the additional linkers are covalently attached to the backbone of the silylated polymer or copolymer. In other embodiments, the linker is covalently attached to a side chain or side group of the polymer or copolymer. In some embodiments, the additional linker is attached via a function group (e.g., an amino group) of a substituted silyl group of the silylated polymer or copolymer, forming a material-linker$_1$-linker$_2$ modified material, wherein the linke$_1$ is a substituted silyl group (a.k.a. heterobifunctional silane crosslinker) such as those discussed herein, and linker$_2$ may be another a second substituted silyl group or another type of linker molecule, such an oligopeptide. In some embodiments, linker$_2$ may formed from the reaction of a terminal amino or a mercapto group on linke$_1$ with EMCS (N—[ϵ-maleimidocaproyloxy]succinimide ester). See Example 2 below.

Further functionalization of the interfacial layer created by, for example, silylation can be achieved by linking the other end of the silyl group or linker$_2$ group to aptamers, including "capture peptides" as discussed further below.

3) Aptamer-Linker-Modified Polymer Backbone

In some embodiments, aptamers, including peptide-based aptamers, may be conjugated to a polymer or copolymer. Peptide aptamers also referred to as "capture peptides" herein, can be used to bind protein targets in the wound environment without inhibiting their signaling capabilities or other functions. Such capture peptides may also be used to capture and increase concentrations of biologically active proteins across a wound bed of a patient, for example, to strengthen or activate a targeted biological response. These and other uses are described in greater detail below.

In some embodiments, a linker is further connected to one or more different types of aptamers, forming a polymer backbone-linker-aptamer conjugate. In some embodiments, the linker is covalently attached to the backbone of the polymer. In other embodiments, the linker is covalently attached to a side group of the polymer. In some embodiments, the aptamer is directly linked to the backbone of the polymer, forming a polymer backbone-aptamer conjugate.

Poloxamer-EMCS-peptide constructs were also successfully used to bind aptamers to a foam. The hydrophobic portion of the poloxamer has strong hydrophobic interactions with the foam. The hydrophilic "arms" has amino groups, which were then linked to oligopeptides using and EMCS linker.

In some embodiments, the aptamer is a computationally selected or phage display derived "capture peptide." Such "capture peptides" may be used to target specific proteins or protein families for binding. One example of such a peptide is P-16, defined by the amino acid sequence GHQGQHIGQMS-AEEAc-Cys-NH$_2$, where the AEEAc-Cys-NH$_2$ is a specially modified C-terminus for conjugation to maleimide groups provided by the EMCS linker. P-16 has been shown to bind to VEGF and PDGF, and potentially other members of the PDGF super-family.

Example 2 below reports the conjugation of an aptamer to 30 PHR chitosan foam via a Sulfo-EMCS ([N-ϵ-maleimidocaproyloxy] sulfosuccinimide ester) crosslinkers.

For example, once bound, the terminal amino group of the 3-aminopropyldiisopropylethoxysilane remains accessible for capture peptide or aptamer binding. In some embodiments biologically active peptides may be bound to this terminal amine group in a manner as to their retain their biological activity. These attached peptides, when the material is used, for example, as part of a dressing, a wound insert or pad, may be used to capture and increase concentrations of biologically active proteins across a wound bed strengthening or activating the targeted biological response. For example, dressings may be prepared to concentrate proteins such as vascular endothelial growth factor in the wound bed, to trigger angiogenesis, and/or to trigger tubule formation. In this manner such materials may be used to better control various biological pathways in a wound environment When a peptide or a factor is attached to the other end of the silane cross linker, it will have a dissociation constant ($K_d$), or binding affinity, that is specific to a given target molecule at a given set of conditions. In some embodiments, it may allow for reversible binding of one or more target(s). In some embodiments, the aforementioned target may be released back into a wound when used as part of the methods and devices contemplated herein. In some embodiments, ingredients may be added to the instillation solution to not only help dissociate the bound factor back into the wound environment but to also interact synergistically with the retained exudate element(s) for a modulating effect so that a favorable wound healing response is elicited. Types of instillation solutions are discussed in greater detail below.

Examples of instilled ingredients which may be used in some embodiments to dissociate bound molecules from the peptide linkers include: saline solutions, solutions with slightly acidic pH, slightly basic pH, solutions with various surfactants (i.e. polysorbate), EDTA or EGTA. In some embodiments, the fluid instilled to initiate the dissociation of the bound factors from the linker will depend upon the binding strength of the factor-linker complex, which is in turn determined by the dissociation constant. The dissociation constant may be modified by using knowledge of amino acid chemistry of the factor of interest to design the linker/peptide/aptamer.

One example of a modified dressing or wound insert is one capable of binding $Ca^{2+}$, wound derived or otherwise, and retaining it at the wound site. During the early phases of wound healing, $Ca^{2+}$ ions are typically released from the cells locally into the extracellular space. The resulting high $Ca^{2+}$ concentration is believed to be a positive effector of many cellular processes involved in wound healing such as adhesion, migration and differentiation. When a high $Ca^{2+}$ concentration is required or is beneficial to the wound bed, instillation or flushing with a solution containing a chelator (e.g., EDTA) may be used to disrupt the binding of $Ca^{2+}$ to the dressing and into the wound bed.

Another factor for use with the current invention is transferrin, a blood plasma protein for iron binding. Chronic wound fluid has been shown to have significantly lower transferrin levels indicating that oxidative stress occurs in chronic wounds. It is known that free iron can play a role in the formation of free radicals. Without being bound by theory, high levels of free iron may contribute to exacerbation of tissue damage and delayed wound healing. Binding and concentrating transferrin onto the dressing can be used to sequester free iron in the wound bed with subsequent release with an appropriate instillation solution and subsequent removal with the exudate following the use of negative pressure. This specific time-dependent modulation of transferring and iron levels can provide a significant benefit to the patient. In an alternate view, the affinity of transferrin for iron is very high but is reversible in that it decreases progressively with decreasing pH below neutrality. If a need for localized iron concentration is necessary, instillation of a low pH solution can be used to unbind or release iron from transferrin.

Hyaluronan, or hyaluronic acid, is another possible target contemplated for use with the current invention. Without being bound by theory, immobilizing and concentrating hyaluronan to the wound bed before instillation with an appropriate solution for release may be used to contribute to keratinocyte proliferation and migration and reduce collagen deposition, which in turn is known to lead to reduced scarring. Hyaluronan is also known for its free-radical scavenging function that could be beneficial as it is bound to the foam on the wound site.

Lactoferrin, known for its antimicrobial and anti-inflammatory properties, is another possible target for some of the embodiments of the present invention. Secreted by endothelial cells, lactoferrin has been shown to have a synergistic effect with FGF2 in that there is a marked increase in their ability together to effect fibroblast migration and proliferation. Specifically designed aptamers can be used to bind both LF and FGF2 and release them with an appropriate instillation solution in an opportune therapeutic timeframe.

TGFB-3 can be another target another possible target for some of the embodiments of the present invention. This protein promotes reorganization of matrix molecules, resulting in an improved dermal architecture and reduced scarring. TGFB-3 is secreted in latent form that requires activation before it is functional. Activation of latent TGFB-3 occurs via binding to thrombospondin-1 (TSP-1). Therefore, TSP-1, may be used in some embodiments, as an ingredients in the instillation fluid to modulate TGFB-3 activity.

Possible other targets include calmodulin, S-100, thyroxine and cholate receptors, amongst many others.

C. USES OF APTAMER MODIFIED MATERIALS

The modified polymers described above and materials made therefrom may be used for a variety of purposes, including to (a) capture and concentrate biological targets in the wound environment, (b) specify the chemical nature of the binding, and/or (c) dictate the orientation with which the target factors are presented to the cells. As discussed in greater detail in the Examples section below, aptamer-modified polyurethanes, including peptide modified Granu-Foam™ (GF), a type of ROCF, may be used to capture specific protein targets in vitro. For example, peptides P16, an anti VEGF peptide, and P22, anti-GM-CSF peptide, were covalently bound to ROCF, and it was demonstrated that these aptamers capture target proteins. Examples 2 and 3 provides results quantifying the amount of GM-CSF captured by ROCF coated with P22, and Example 4 presents results quantifying the amount of VEGF captured by ROCF coated with P16.

In some embodiments the aptamer-modified polymers may be used to bind protein targets in the wound environment without inhibiting their signaling capabilities or other functions. Such aptamer-modified polymers may be used as part of a dressing or wound insert, for example, to capture and increase concentrations of biologically active proteins across a wound bed of a patient, for example, to strengthen or activate a targeted biological response.

In some embodiments, such a dressing may be used to concentrate proteins of interest such as vascular endothelial growth factor in the wound bed to trigger angiogenesis and tubule formation. Additionally, peptides may be designed to antagonize or sequester proteins that adversely affect the healing process, such as matrix metalloproteinases. Dressings made of such aptamer-modified polymers may thus be used, in some embodiments, to modulate various biological pathways or to manage the presence of unwanted bioactive molecules or enzymes in the wound environment.

In addition to dressings, aptamer-modified polymers, including those using a heterobifunctional silyl-modified linker and a polyurethane-based polymer or copolymer, may also be used in a wide array of other materials, matrixes and biomedical devices, including catheters. In such embodiments, they may be used to conjugate a variety of aptamers, or other compounds, including antimicrobials. The application of these materials to a negative pressure-based therapy is discussed in greater detail below.

Materials of this invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts:Properties, and Use* (2002), which is incorporated herein by reference.

D. PREPARATION OF INSERTS COMPRISING FOAM MATERIALS BASED

In another aspect, foam-based polymers may be physically and/or chemically treated, coated or manipulated before or after they are covalently linked to an aptamer. Some embodiments of making modified wound inserts comprise: compressing (and/or felting) at least a portion of a foam. Some embodiments comprise: treating (e.g., by applying heat, or activating a coating that has been applied to) the compressed foam such that the foam remains substantially compressed in the absence of an external compressive force. For example, in some embodiments, treating comprises heating the foam (e.g., foam) to an elevated temperature sufficient to reduce resiliency of the foam. For example, the foam can be heated to a temperature at which resiliency of the foam is reduced and/or relaxed, but that is below the melting temperature of the foam (e.g., such that the foam is not degraded by the elevated temperature). In this way, the foam can be compression set using heat and pressure (compressive force) to relax compressive strains developed in the foam. Generally, high temperatures are used to achieve the compression set. To achieve the desired "set" such that resiliency of the foam is reduced and/or the foam remains substantially compressed in the absence of a compressive force, temperatures can range from 158 degrees Fahrenheit to 482 degrees Fahrenheit (e.g., equal to, less than, greater than, or between any of: 140, 160, 180, 200, 220, 240, 260, 280, 300, 320, 340, 360, 380, 400, 420, 440, 460, 480, 500 degrees Fahrenheit, depending upon the particular foam used). The foam may also be put through a cooling cycle to help retain the set introduced. For example, the foam may be cooled to a temperature below room or ambient temperature (e.g., to or in a temperature equal to, less than, greater than, or between any of: 0, 5, 10, 15, 20, 25, 30, 35, 40, 45, 50, 55, 60, 65, or 70 degrees Fahrenheit). In some embodiments of the present methods of forming a modified wound insert, the foam is disposed between two heated plates or platens (e.g., in a plate or platen press and/or where the plates are heated to a temperature sufficient to reduce the resiliency of the foam); and the press is actuated to move the plates toward one another (e.g., perpendicular to thickness 320 of thick portions 304) such that the foam is compressed to the desired overall thickness or degree of compression). Such a press can be electrically, mechanically, and/or hydraulically operated.

Some embodiments of the present methods of making modified wound inserts also comprise: cooling the foam (e.g., after heating the foam) such that the compressed portion of the foam remains substantially compressed at room temperature (e.g., at a temperature of 72 degrees Fahrenheit) in the absence of a compressive force. In other embodiments, cooling the foam includes cooling a coating that has been applied to the foam such that the compressed portion remains substantially compressed in the absence of a compressive force at a temperature or temperature range equal to, less than, greater than, or between any of: 10, 20, 30, 40, 50, 60, 70, 80, 90, 100, 110, 120, 130, 140, and/or 150 degrees Fahrenheit.

Thick and thin regions in the foam can be formed by any suitable methods, such as, for example, laser cutting or the like. Such methods are taught, for example, by U.S. Patent Application Publication 2011/0178451, which is incorporated herein by reference.

In such embodiments, the coating can be dispersed through the foam, such as, for example, by spraying the foam with the coating, dipping the foam in the coating, and/or any other suitable way of dispersing the coating in the foam. In some embodiments, for example, the foam can be coated with a material that has a transition temperature (e.g., melting point, glass transition, etc.) that occurs at a relatively low temperature (e.g., lower than the foam alone), or that develops stiffness as it dries. In some embodiments, the coating can be configured to enable the foam to be compressed (and/or compression set) at lower temperatures (e.g., without heating), such that the coating becomes stiff or otherwise resistant to expansion as it cools or dries to hold the foam in its compressed configuration. For example, a fluid adhesive may be applied to thick portions before compressing the foam and permitted to dry before removing the compressive force, such that the dried adhesive will resist expansion from the compressed thickness. In other embodiments, the coating can be configured to compression set the foam such that the compression is reversible (e.g., at least partially and/or completely reversible) such that the foam can expand (e.g., after placing in or on a wound) as it warms or absorbs water. In some embodiments, the coating comprises a cross-linkable polymer and/or activating comprises exposing the coating to light and/or elevated temperature (e.g., above ambient temperature, such as, for example, a temperature sufficient to cause at least part of the cross-linkable polymer to cross-link) to cause at least some portion of the cross-linkable polymer to become modified.

Examples of suitable coatings include cross-linkable polymers that contain n-methylol acrylamide (NMA). NMA is a monomer that may be co-polymerized with many other monomers (such as acrylics & vinyls). On heating, (e.g., to about 140° C.), NMA reacts with itself and other hydroxyl-containing groups (e.g., carboxyl). Similarly, urea formaldehyde, melamine formaldehyde, and/or phenol formaldehyde can be caused to react with themselves and other hydroxyl-containing polymers to form crosslinks. Other crosslinking agents may include, for example, modified ethylene ureas, which react with hydroxyl-containing polymers at elevated temperatures to crosslink them. Other crosslinking agents can include peroxides which will crosslink most polymers at elevated temperatures. Polymers containing hydroxyl and carboxyl groups may also be combined, and, when heated, may form polyester crosslinks. Additionally, epoxy prepolymers can be used that have low reactivity at room temperatures, and when heated, react quickly to form an epoxy polymer with crosslinks. Similarly, polymeric isocyanates may be used that will only react significantly fast at elevated temperatures and in presence of hydroxyl groups, amines, or moisture to form polyurethanes or polyureas.

In some embodiments, a combination of high-density regions and low-density regions cooperate to provide various characteristics for the present modified wound inserts. For example, the high-density regions have a smaller aggregate cell size and increased cell density, such that the high-density regions have improved wicking function and more-effectively transmit fluid (e.g., draw fluids away from the wound surface and/or communicate fluid from a fluid source to the wound surface more effectively than the low-density regions. The high-density regions are generally also mechanically stronger than the low-density regions, such that the high-density regions can provide structural support for the low-density regions and/or the modified wound insert as a whole (e.g., such that the modified wound insert is resistant to tearing in directions that are not parallel to the low-density regions). Additionally, the low-density regions have a larger effective cell or pore size such that the low-density regions are less-susceptible to clogging. Especially when a negative pressure is applied to draw fluid and/or exudate away from the wound and through the modified wound insert, the larger pore size of the low-density regions may permit fluids to be drawn through the low-density regions at a higher velocity than the fluid is drawn through the high-density regions, such that particulate and granular matter are drawn to and/or through the low-density to discourage and/or decrease the likelihood of clogging in the high-density regions. In some embodiments, the foam can also be coated with a hydrophilic material to improve wicking properties of the modified wound insert.

The low-density regions may also be configured to permit the wound dressing to bend and/or otherwise conform to a wound. For example, the low-density regions can be relatively easier to bend (and/or less resilient when the modified wound insert is bent or folded along a low-density region) such as to double over a modified wound insert, and/or to conform a modified wound insert to additional hardware such as plates, pins, or the like.

Typical single-density foam modified wound inserts are isotropic such that under negative pressure, a typical single-density foam modified wound insert will contract proportionally in all directions. In some embodiments, the present modified wound inserts may also be configured to be anisotropic, such that the present modified wound inserts can be configured to mechanically assist with wound closure. For example, low-density regions are less-dense (and will compress more under negative pressure) than high-density regions. As such, if negative pressure is applied to modified wound insert, low density regions will contract more than high-density regions, such that high-density regions will be drawn together and modified wound insert will contract laterally more than longitudinally. In other embodiments, the present modified wound inserts can be configured to have alternating and sequentially larger closed ring-shaped high-density regions and low-density regions, such that under negative pressure, the modified wound insert will contract laterally inward to its own center.

In some embodiments, thick portions, thin portions, high-density regions, and/or low-density regions can be coated and/or printed (either before or after compression) to enhance the hydrophilic or hydrophobic properties of individual regions of the foam or of the foam as a whole. Such coated regions may also contain and/or be coated with other additives, such as antibiotics, or blockage-reducing agents.

In some embodiments of the present invention, wound dressings comprise a wound dressing configured to be positioned on a wound (e.g., 26) of a patient (e.g., 30) and/or on or in contact with the wound surface (e.g., 42).

Some embodiments of the present wound-treatment methods comprise: positioning a modified wound insert (e.g., any of the present modified wound inserts such as 34a, 34b) on a wound (e.g., 26) of a patient (e.g., 30), where the modified wound insert comprises a foam (e.g., 300) having high-density regions (e.g., 404) and low-density regions (e.g., 408) having a density that is less than the density of the high-density regions. In some embodiments, the foam is sterile (e.g., substantially free of microbes and/or bacteria). Some embodiments further comprise: coupling a drape (e.g., 38) to skin (e.g., 46) adjacent the wound such that the drape covers the modified wound insert and the wound, and forms a space between the drape and the wound. Some embodiments comprise: applying negative pressure to the wound through the wound dressing (e.g., through the modified wound insert). In some embodiments, applying negative pressure to the wound comprises activating a vacuum source (e.g., apparatus 14 of FIG. 1, or vacuum source 200 of FIG. 3) that is coupled to the wound dressing. Some embodiments comprise: delivering a fluid to the wound through the wound dressing. In some embodiments, delivering a fluid comprises activating a fluid source (e.g., fluid source 248 of FIG. 3) that is coupled to the wound dressing.

Some embodiments of the present wound-treatment systems comprise either embodiment of system 10 (or any subset of components of either embodiment of system 10), and one or more of the present modified wound inserts and/or wound dressings.

The various illustrative embodiments of devices, systems, and methods described herein are not intended to be limited to the particular forms disclosed. Rather, they include all modifications and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

It will be understood that the benefits and advantages described above may relate to one embodiment or may relate to several embodiments. It will further be understood that reference to 'an' item refers to one or more of those items, unless otherwise specified.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the scope of this invention.

E. DEVICES COMPRISING AN APTAMER-MODIFIED WOUND INSERT

The aptamer-modified polymers described above and materials made therefrom may be used for a variety of purposes, including to (a) capture and concentrate biological targets in the wound environment, with the option to release back into the wound bed, (b) specify the chemical nature of the binding, and/or (c) dictate the orientation with which the target factors are presented to the cells.

A dressing or wound insert made for an aptamer-modified polymer may be used together with negative pressure wound therapy. In some embodiments, compatible foam coated with aptamers or small peptide linkers (ligands) which select for beneficial molecules in the wound fluid as it passes through the foam would thereby prevent their removal into the negative pressure wound therapy canister. Appropriate molecules for selection from wound fluid include metabolites, growth factors, chemokines and cytokines which would not impede fluid flow through the negative pressure wound therapy dressing. In some embodiments, appropriate linkers would bind the wound fluid molecules in such an orientation that the "active site" of the wound fluid molecule is still available for eliciting a biological response. For example, one such molecule may be VEGF. VEGF has specific sites on the molecule that bind to cellular receptors. The binding of the VEGF molecule to the cellular receptor may be used to initiate a biological response, typically angiogenesis.

Figure 15:
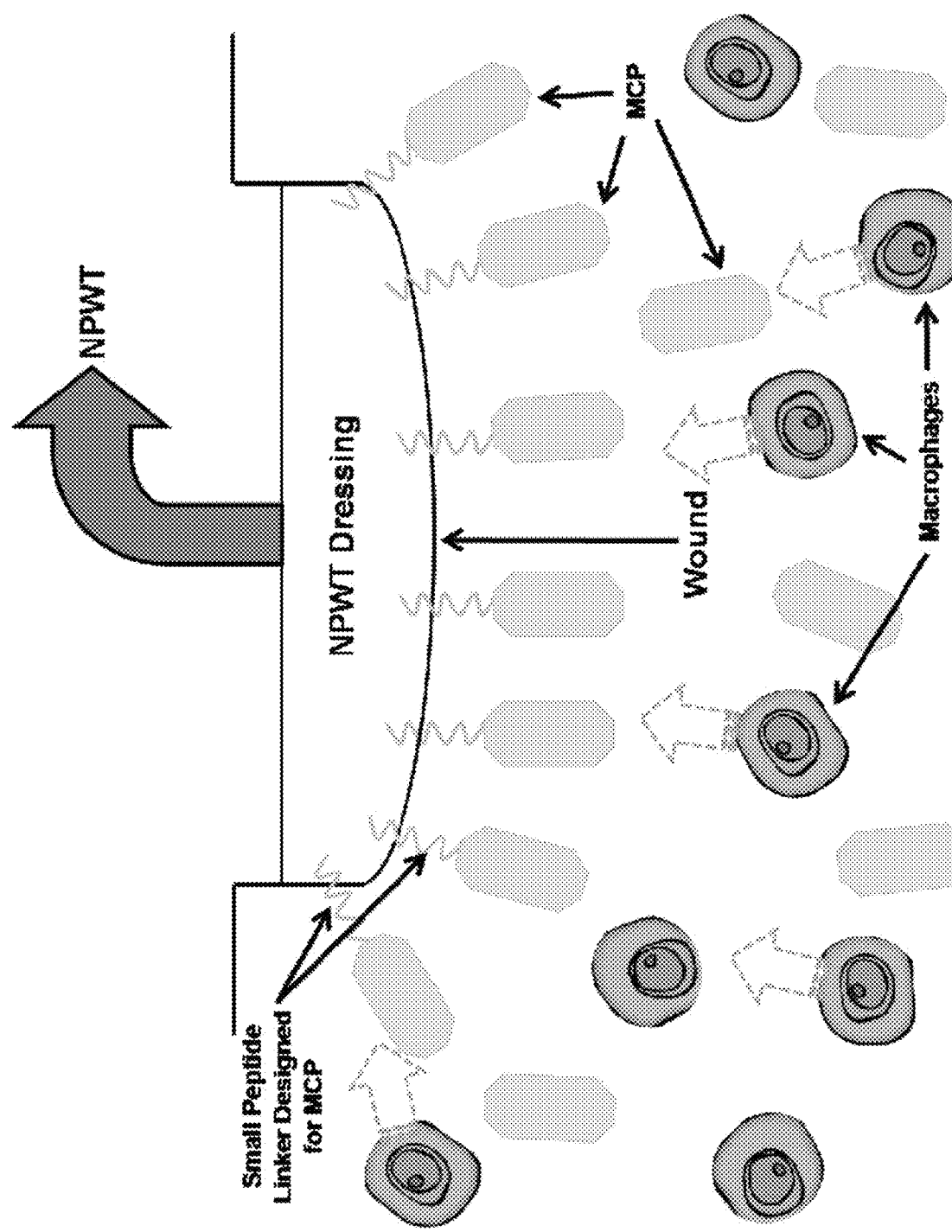
FIG. 15 shows an aptamer modified polymer used in a dressing used in conjunction with negative pressure wound therapy (NPWT). In this embodiment, the aptamer is selective for MCP1, a chemotactic molecule to macrophages. Such a modified dressing may be used to stimulate macrophage migration into the wound and thereby progress the wound from a chronic to a healing state.
Figure 16:
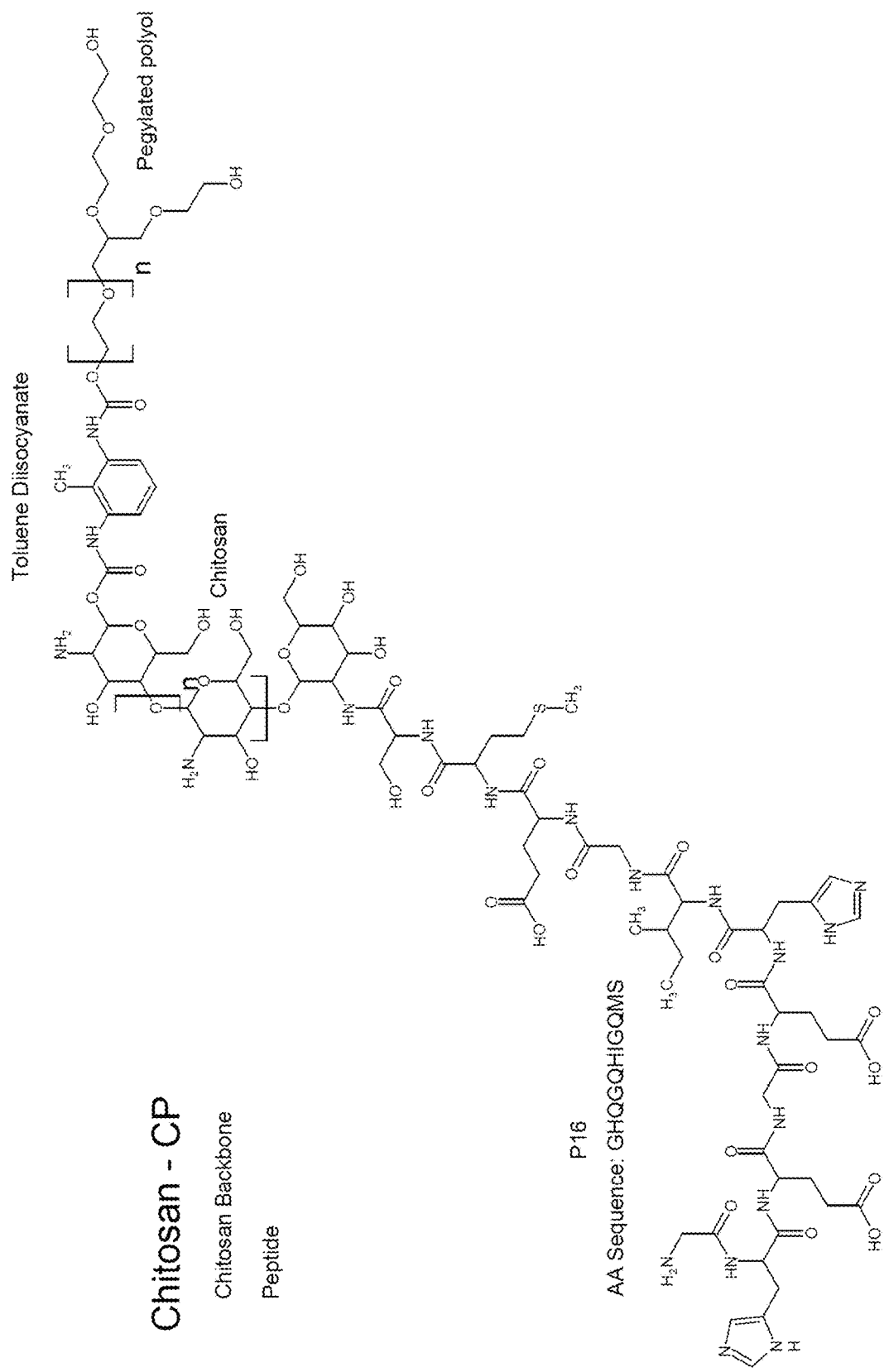
FIG. 16 provides structure and connectivity information for a portion of an aptamer-modified polymeric foam embodiment comprising an oligopeptide (P16; SEQ ID NO: 2) covalently attached to a polyurethane-copolymer based on a PEGylated triol, a toluene diisocyanate and a chitosan oligomer.
Figure 17:
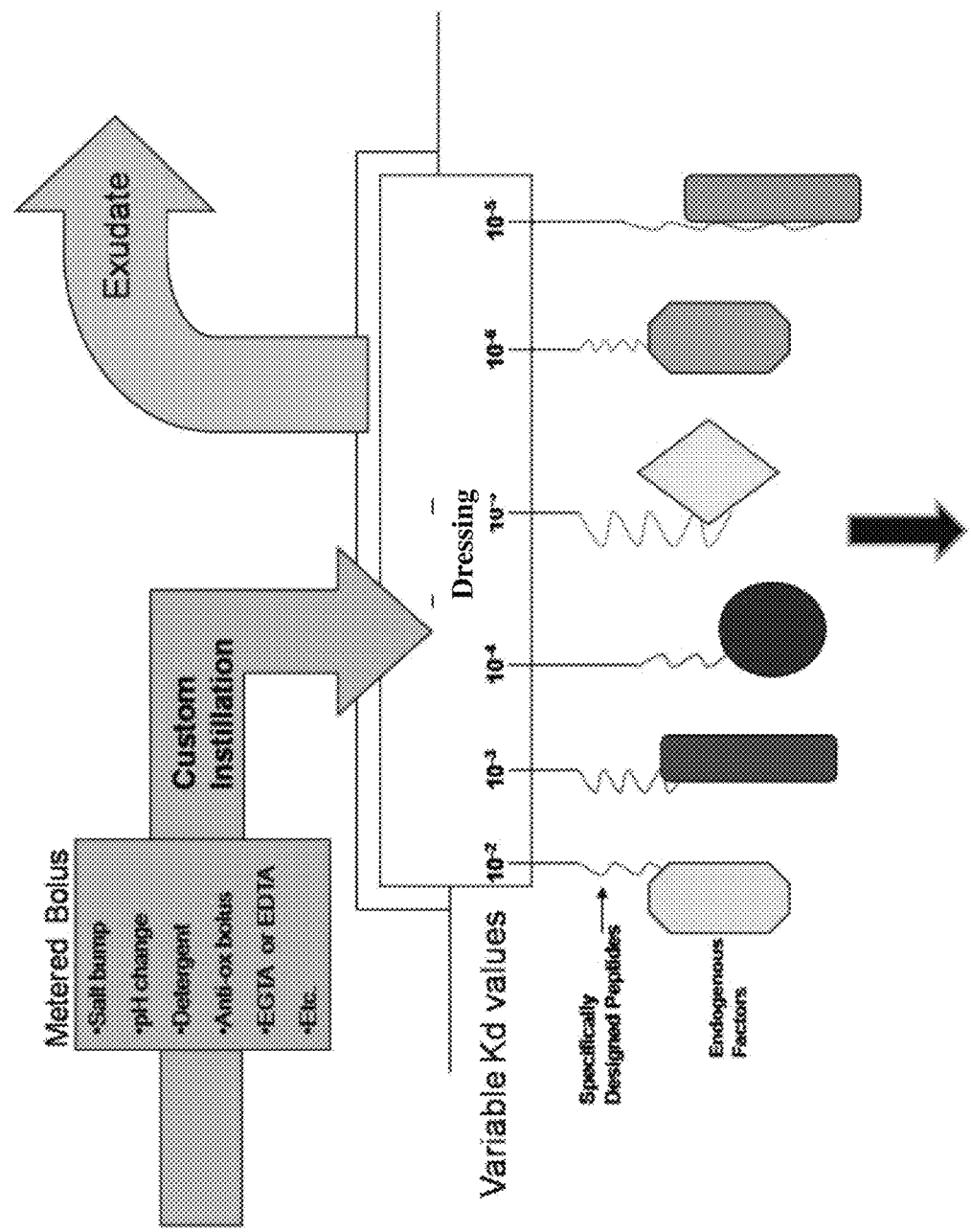

In some embodiments, the methods taught herein may be used to bind to molecules chemotactic to macrophages such as MCP1 (FIG. 15), which may be used to stimulate macrophage migration into the wound and thereby progress the wound from a chronic to a healing state. In some embodiments, PDGF or collagen fragments could be bound during the proliferative or late inflammatory phases to stimulate the migration of fibroblasts into the wound. Stimulating the migration of macrophages and then fibroblasts into the wound may assist in the progression of the wound through the inflammatory phase and into the proliferative phase of wound healing. In some embodiments, Nitric Oxide Synthase could be bound from the wound fluid to stimulate perfusion. This may help to promote healing by allowing a higher level of nutrients into the wound. In some embodiments, anti-inflammatory cytokines such as IL4 or IL10 could be bound to decrease inflammation, thus progressing the wound more quickly through the inflammatory and into the proliferative phase of healing. DNA fragments could also be bound to the dressing. In some embodiments, the binding of highly charged DNA could enable current to be passed through the dressing. Electrical stimulation has been used for many years in the treatment of wounds. Therefore, binding DNA to the wound dressing may allow for the application of current to the wound.

Figure 18:
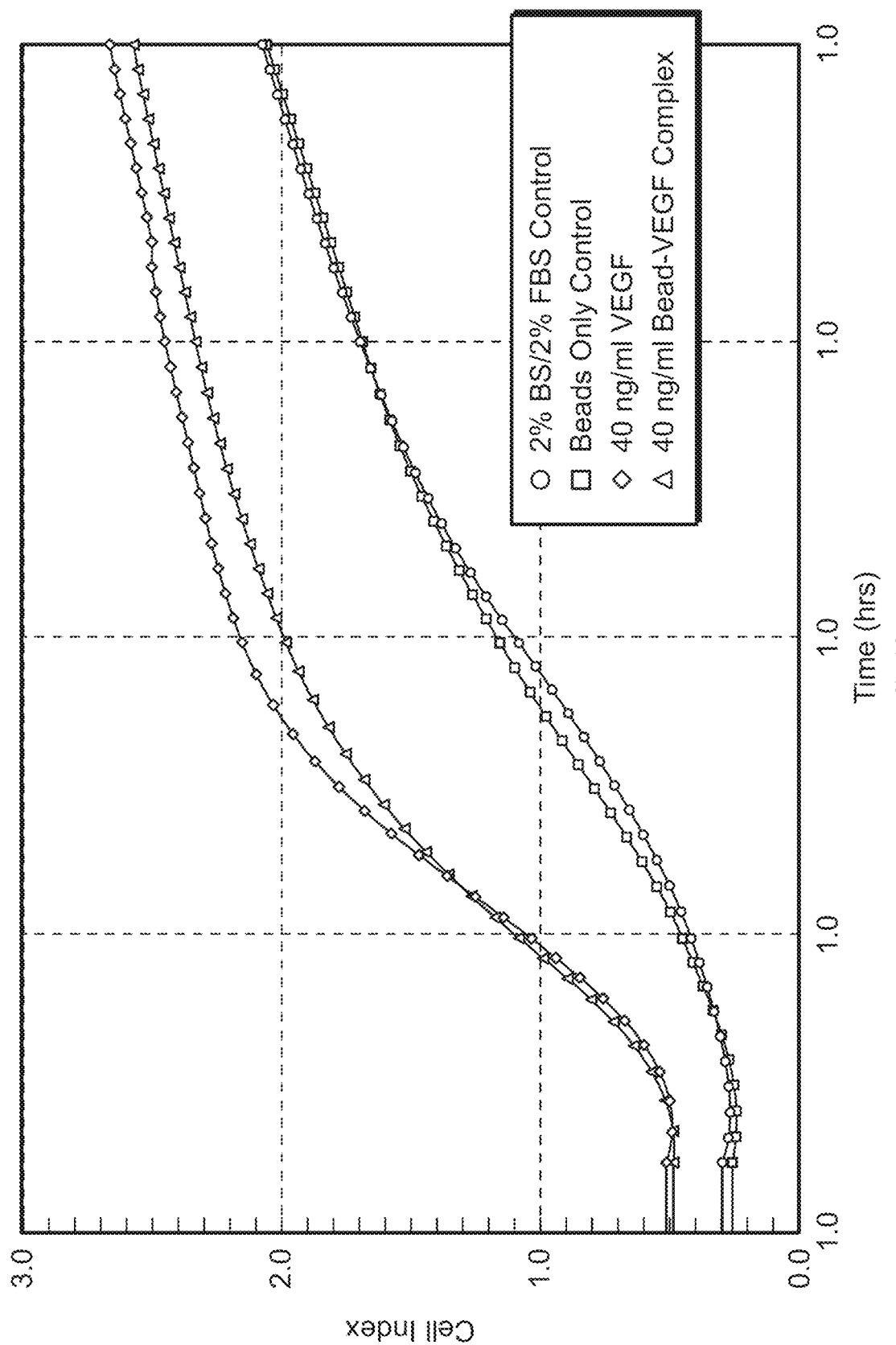
FIG. 18—VEGF in solution was passed over beads linked to an anti-VEGF antibody. After passing the solution over the beads, beads were spun down and washed. The washed beads were then used for endothelial cell migration assays. Results from this experiment showed that after 3 hours, 2 fold more cells had migrated towards the beads bound to the antibody (and VEGF) than beads with no antibody.

Experiments were conducted whether aptamers bound to a peptide (in this case an antibody) could still maintain biological activity. VEGF in solution was passed over beads linked to an anti-VEGF antibody. After passing the solution over the beads, beads were spun down and washed. The washed beads were then used for endothelial cell migration assays. Results from this experiment showed that after 3 hours, 2 fold more cells had migrated towards the beads bound to the antibody (and VEGF) than beads with no antibody. See FIG. 18. Thus, it was shown VEGF bound to an antibody can maintain biological activity.

Referring now to the drawings, and more particularly to FIG. 1, shown therein is an embodiment of one of the present wound treatment system 10. In the embodiment shown, apparatus 10 comprises a wound-treatment apparatus 14, and a wound dressing 18 coupled to apparatus 14 by a conduit 22. As shown, dressing 18 is configured to be coupled to (and is shown coupled to) a wound 26 of a patient 30. More particularly, in the embodiment shown, dressing 18 comprises a modified wound insert 34 and a drape 38. As shown, modified wound insert 34 is configured to be positioned (and is shown positioned) on wound 26 (e.g., on or adjacent to wound surface 42), and/or drape 38 is configured to be coupled to (and is shown coupled to) skin 46 of the patient adjacent to wound 26 such that drape 38 covers modified wound insert 34 and wound 26, and forms a space 50 between drape 38 and wound 26 (e.g., wound surface 42).

Apparatus 14 can comprise, for example, a vacuum source configured to be actuatable (and/or actuated) to apply negative pressure (e.g., via conduit 22) to wound dressing 18, a fluid source configured to be actuatable (and/or actuated) to deliver (e.g., via conduit 22) a fluid (e.g., an installation fluid such as a medicinal fluid, antibacterial fluid, irrigation fluid, and or the like) to wound dressing 18. System 10 can be implemented and/or actuated and/or coupled to patient 30 in any of various configurations and/or methods similar to those described in the prior art. For example, various wound therapy systems and components are commercially available through and/or from KCI USA, Inc. of San Antonio, Tex., U.S.A., and/or its subsidiary and related companies (collectively, "KCI").

Conduit 22 can comprise a single lumen conduit (e.g., switched between a vacuum source and/or a fluid source and apparatus 14), or can comprise multiple single-lumen conduits or a multi-lumen conduit such that, for example, fluid can be delivered and/or negative pressure can be applied to wound dressing 18 individually and/or simultaneously. Additionally, conduit 22 can comprise, for example, a first lumen for the application of negative pressure and/or fluid delivery, and at least one additional lumen for coupling to pressure sensor(s) to sense pressure or negative pressure between drape 38 and surface 42. In some embodiments, conduit 22 can comprise multiple lumens (e.g., as in a single conduit with a central lumen for application of negative pressure and/or fluid delivery, and one or more peripheral lumens disposed adjacent or around the central lumen such that the peripheral lumens can be coupled to a pressure sensor to sense a pressure or negative pressure between drape 38 and surface 42 (e.g. in space 50). The lumens may be arranged with a central lumen and other lumens disposed radially around the central lumen, or in other suitable arrangements. The lumens may also be provided in separate conduits. In the embodiment shown, system 10 further comprises a wound dressing connection pad 54 configured to be coupled (and is shown coupled) to conduit 22. One example of a suitable connection pad 54 is the "V.A.C. T.R.A.C.® Pad," commercially available from KCI. One example of a suitable drape 38 includes the "V.A.C.® Drape" commercially available from KCI.

Figure 2:
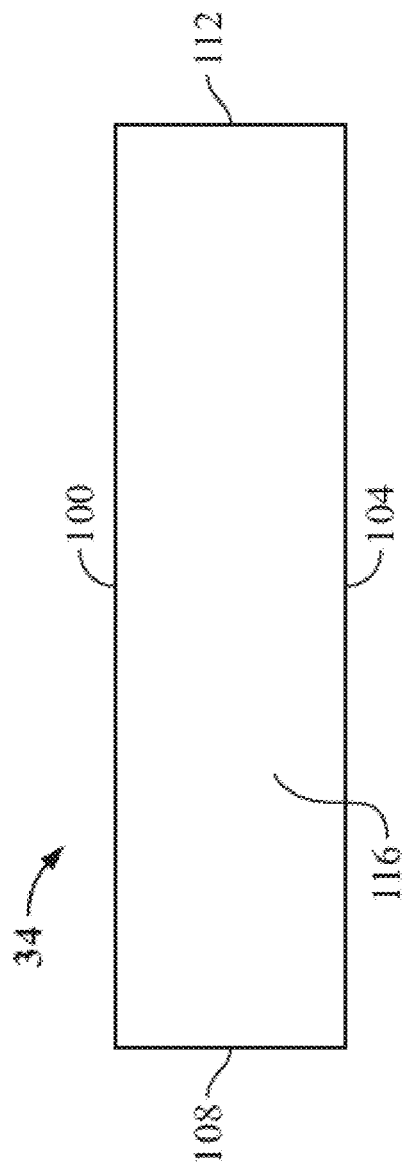
FIG. 2 depicts an enlarged side view of the modified wound insert of FIG. 2.

Referring now to FIG. 2, a side view of a modified wound insert 34 is shown. Modified wound insert 34 has an upper side 100, a lower side 104, lateral sides 108, 112 and interior volume 116. Although only one side is shown of modified wound insert 34, it will be understood by those of ordinary skill in the art that modified wound insert 34 includes a three-dimensional rectangular volume having a depth extending perpendicular to the side shown. In other embodiments, modified wound insert 34 can have any suitable shape, such as, for example, a round cylindrical shape, a fanciful shape, or may be trimmed to fit an irregular shape of a wound (e.g., 26 and/or wound surface 42). Modified wound insert 34 can comprise a foam, such as, for example, open-celled foam (which may also be reticulated).

Embodiments of the present wound treatment methods may be better understood with reference to FIG. 1, which depicts a schematic block diagram of one embodiment of system 10. In the embodiment shown, wound dressing 18 is coupled to apparatus 14, and apparatus 14 comprises a vacuum source 200 (e.g., a vacuum pump and/or the like) coupled to a canister 204 (e.g., configured to receive exudate and or the like from wound dressing 18) by way of a conduit 208. In the embodiment shown, apparatus 14 further comprises: a pressure sensor 212 having a first pressure transducer 216 coupled to conduit 208 by way of conduit 220 and/or tee-fitting 224, and a second pressure transducer 228 coupled to canister 204 and/or wound dressing 18 by way of conduit 232. Pressure sensor 212 is configured to sense the negative pressure in wound dressing 18, and/or any of the various lumens (e.g., within conduits) coupled to wound dressing 18, pressure sensor 212, and/or vacuum source 200.

In the embodiment shown, apparatus 14 further comprises a pressure release valve 236 coupled to conduit 232. Further, in the embodiment shown, canister 204 and vacuum source 200 are coupled to wound dressing 18 by way of conduit 240; and/or canister 204 can comprise a filter 244 at or near an outlet of canister 204 to prevent liquid or solid particles from entering conduit 208. Filter 244 can comprise, for example, a bacterial filter that is hydrophobic and/or lipophilic such that aqueous and/or oily liquids will bead on the surface of the filter. Apparatus 14 is typically configured such that, during operation, vacuum source 200 will provide sufficient airflow through a filter 244 that the pressure drop across filter 244 is not substantial (e.g., such that the pressure drop will not substantially interfere with the application of negative pressure from wound dressing 18 from vacuum source 200).

In the embodiment shown, apparatus 14 further comprises a fluid source 248 coupled to wound dressing 18 by way of a conduit 252 that is coupled to conduit 240 such as, for example, by way of a tee- or other suitable fitting 256. In some embodiments, tee fitting 256 can comprise a switch valve and/or the like such that communication can be selectively permitted between wound dressing 18 and vacuum source 200, or between wound dressing 18 and fluid source 248. In some embodiments apparatus 14 comprises only one of vacuum source 200 and fluid source 248. In embodiments of apparatus 14 that comprise only fluid source 248, canister 204 and/or pressure sensor 212 can also be omitted. In various embodiments, such as the one shown, conduit 232 and/or conduit 240 and/or conduit 252 can be combined and/or comprised in a single multi-lumen conduit, such as is described above with reference to FIG. 1. In some embodiments, fluid source 248 is coupled directly to wound dressing 18 (e.g., conduit 252 is coupled one end to wound dressing 18, such as via connection pad 54, and conduit 252 is coupled on the other end to fluid source 248; and conduit 252 is not coupled to tee fitting 256).

Figure 3:
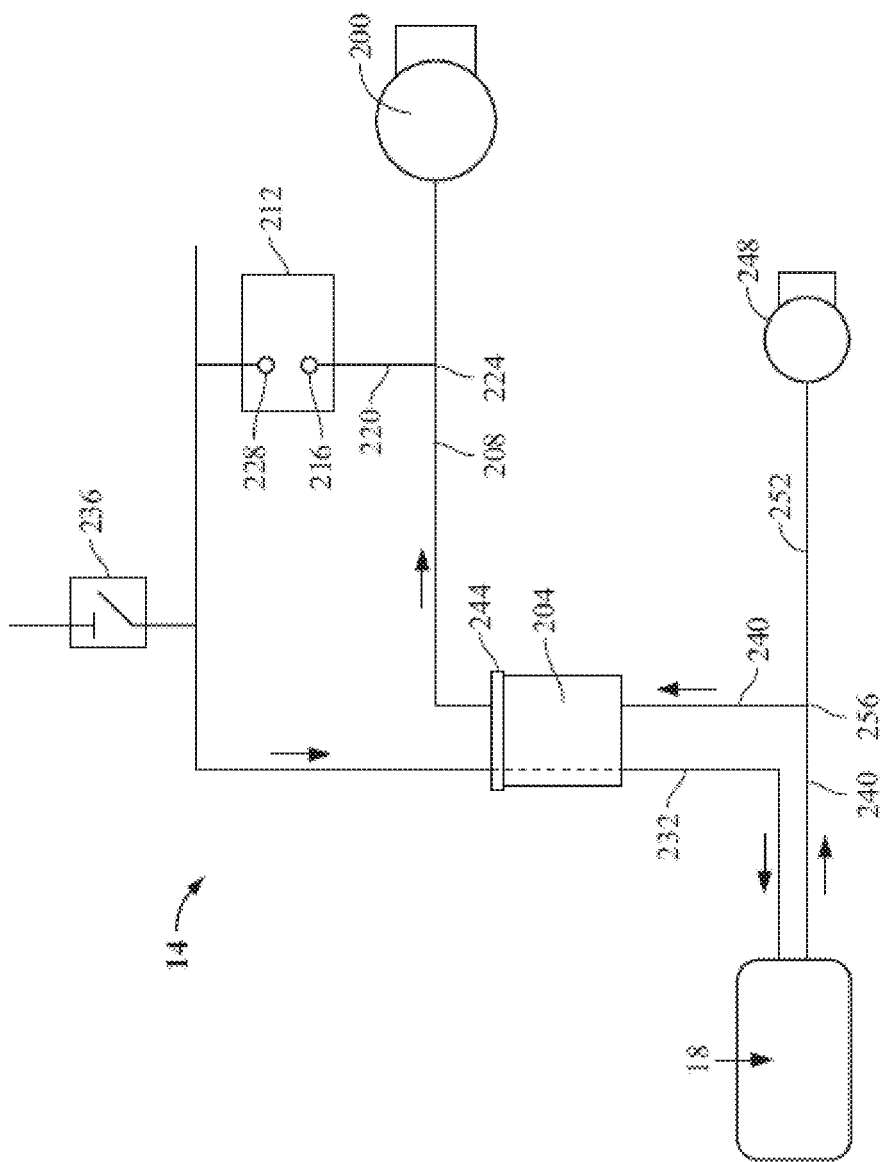
FIG. 3 depicts a schematic block diagram of one embodiment of a wound treatment apparatus that can comprise and/or be coupled to and/or be used with the present wound dressings and/or modified wound inserts.
Figure 4:
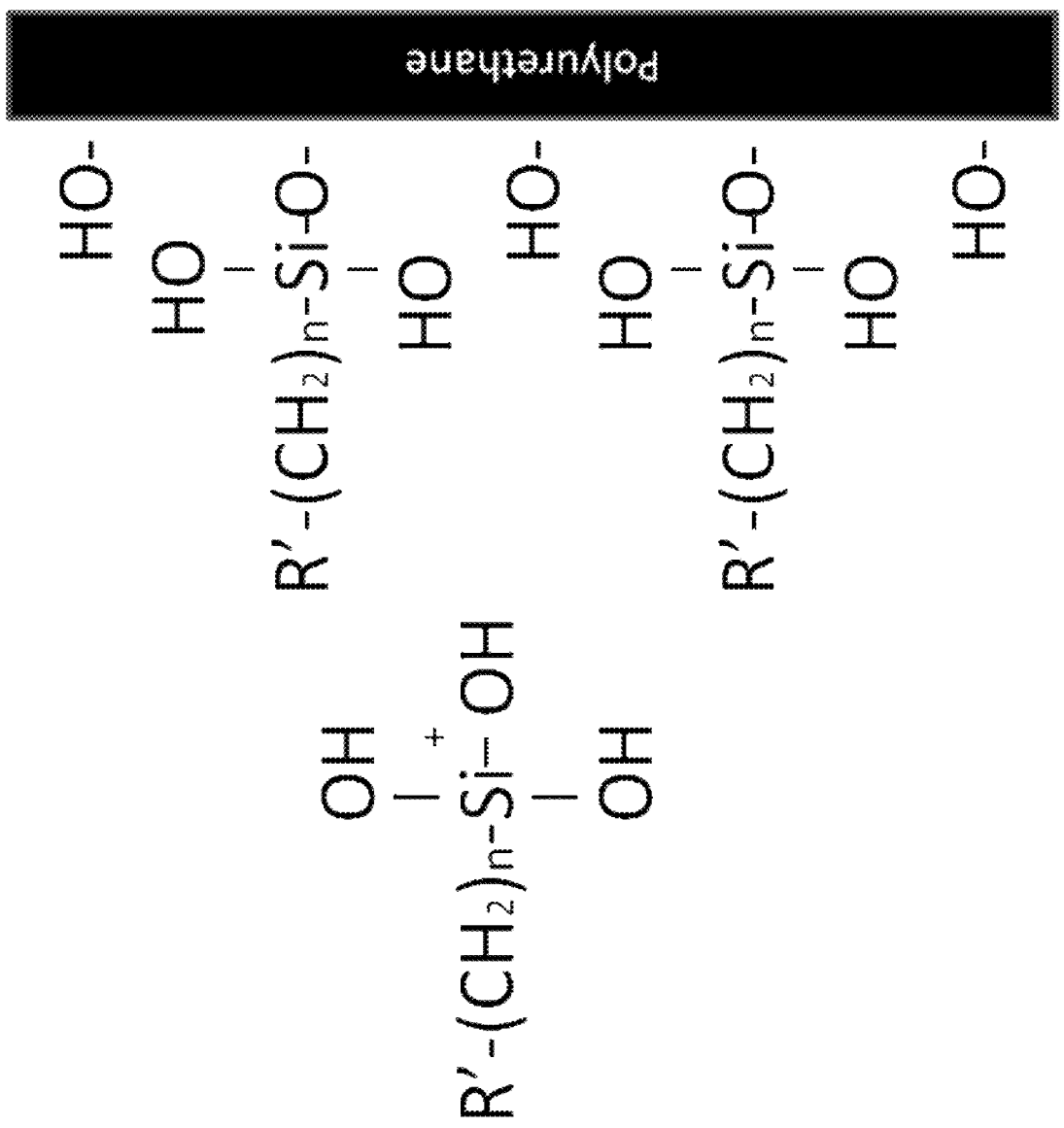
FIG. 4 depicts a schematic diagram according to some embodiments of the present invention. In this side view, a polyurethane-based polymer having free hydroxy groups is modified with a R'—$(CH_2)_n$—$Si(OH)_3$ reagent.

In various embodiments, such as the one shown in FIG. 3, apparatus 14 can be configured such that as soon as liquid in the canister reaches a level where filter 244 is occluded, a much-increased negative (or subatmospheric) pressure occurs in conduit 208 and is sensed by transducer 216. Transducer 216 can be connected to circuitry that interprets such a pressure change as a filled canister and signals this by means of a message on an LCD and/or buzzer that canister 204 requires emptying and/or replacement, and/or that automatically shuts off or disables vacuum source 200.

Apparatus 14 can also be configured to apply negative (or subatmospheric) pressure (e.g., continuously, intermittently, and/or periodically) to the wound site, and/or such that pressure relief valve 236 enables pressure at the wound site to be brought to atmospheric pressure rapidly. Thus, if apparatus 14 is programmed, for example, to relieve pressure at ten-minute intervals, at these intervals pressure relief valve 236 can open for a specified period, allow the pressure to equalize at the wound site, and then close to restore the negative pressure. It will be appreciated that when constant negative pressure is being applied to the wound site, valve 236 remains closed to prevent leakage to or from the atmosphere. In this state, it is possible to maintain negative pressure at the wound site without running and/or operating pump 200 continuously, but only from time to time or periodically, to maintain a desired level of negative pressure (i.e. a desired pressure below atmospheric pressure), which is sensed by transducer 216. This saves power and enables the appliance to operate for long periods on its battery power supply.

In some embodiments, factors may be removed, or their concentration modulated, using electrical pulses, light, ultrasound and temperature.

F. INSTILLATION SOLUTIONS

In some embodiments dressing made from the aptamer modified poloymers disclosed herein may be used together with wound instillation solutions, for example in the application of a negative pressure treatment to a patient's wound. In some embodiments, the instillation solution comprises ingredients to help release or modulate the release of the factors bound to the foam.

Examples of instilled ingredients which may be used in some embodiments to dissociate bound molecules include: saline solutions, solutions with slightly acidic pH, solutions with slightly basic pH, solutions with various surfactants (i.e. polysorbate), solutions with slight ionic charge, EDTA or EGTA. In some embodiments, the fluid instilled to initiate the dissociation of the bound factors from the linker will depend upon the binding strength of the factor-linker complex, which is in turn determined by the dissociation constant. The dissociation constant may be modified by using knowledge of amino acid chemistry of the factor of interest to design the linker/peptide.

In some embodiments, the instillation solution comprises hypochlorous acid (HOCl) and hypochlorite ion. Both are examples of effective antimicrobial agents for biocidal action. For example, HOCl is typically capable of killing a broad spectrum of microbes (e.g., fungus, bacteria, viruses, fungus, yeast, and the like); often in a relatively short period of time (e.g., is capable of killing greater than 99% of microbes within a period of less than 10 seconds). Such antimicrobial agents can be generated or formed by a combination of the present reactive agents and fluid (e.g., water and/or aqueous solution, such as, for example, saline solution) and may be more effective and/or more versatile than antibiotics and other commonly used antimicrobial agents used in wound treatment in the past. For example, antibiotics may be bacteria-specific such that testing may be required to determine a suitable antibiotic to use for a specific wound or infection; and/or such that antibiotics may have only limited effectiveness for individual wounds and/or infections (e.g., where testing is not performed and/or where a wound is infected with a plurality of different bacteria). Such testing may take as long as several days to determine an appropriate antibiotic, delaying treatment or selection of an effective antibiotic. Additionally, bacteria may develop resistance to antibiotics, such that antibiotics may have reduced effectiveness after an amount of time. Further, antibiotics are typically administered intravenously (systemically) such that antibiotics may kill beneficial bacteria (e.g., in a patient's digestive system) and/or may cause organ damage (e.g., to a patient's liver).

In contrast, the reactive agents (and/or antimicrobial products of the reactive agents) of the present embodiments can be configured to have a broad-spectrum killing power that will kill a variety of microbes (e.g., fungus, bacteria, viruses, fungus, yeast, etc.). Additionally, the present reactive agents (and/or antimicrobial products of the reactive agents) can be delivered locally (preventing systemic damage or other side effects to organs and the like).

However, due to the reactivity of HOCl or OCl$^-$ with oxidizable organic substances, its utility in wound care applications has previously been limited. For example, prior art methods of generating hypochlorous acid have required electrolysis of saltwater or the like (e.g., with expensive equipment at a patient's bedside). By way of another example, commercially available chemicals (e.g., bleach) have a hypochlorous acid concentration of 5% or greater, which is too high to permit medical uses (e.g., will cause cytoxicity). Additionally, at suitable medical concentrations (e.g., 2-20 mM hypochlorous acid solutions), approximately 99% or more of the solution is water, such that shipping is more expensive and/or more difficult than necessary. Further, storage of hypochlorous acid solutions is difficult, as reactions with containers typically degrade or reduce the concentration of the hypochlorous acid solution. However, the present wound inserts can be deposited with reactive agents (have reactive agents deposited in the foam of the wound inserts) such that upon application of a fluid such as saline or water, OCl (and/or ClO⁻) is released (e.g., to form hypochlorous acid) and delivered to a wound for biocidal action.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation and Silanation of 30 PHR Chitosan Interfacial Layer

In this procedure, a heterobifunctional silane crosslinker, 3-aminopropyldiisopropylethoxysilane, was deposited on 30 per hundred resin (30 phr) chitosan foam, which was produced using 0.3 g of chitosan (Sigma Product Number 448877) per 1.0 g of an aromatic diisocyanate and tri-branched polyol mix. A plurality of the —OH groups of the copolymer were then silylated with 3-aminopropyldiisopropylethoxysilane (Gelest™ compound SIA0602.0). This was accomplished using the protocol further below.

The resulting silylated 30 phr chitosan foam was compared with silylated reticulated open cell foam using an o-phtaldialdehyde (OPA) assay that compares relative fluorescence units (RFU). OPA fluoresces when it binds to primary —$NH_2$ groups. Therefore, RFUs for 30 phr chitosan foam should be greater than, for example, OPA alone indicating the presence primary of —$NH_2$. The results from this test are shown in Table 1 below and in FIG. 5. This quantitative analysis demonstrated that the silylated 30 phr chitosan foam ("30 PHR Si") had relatively twice the number (1.25e7) of RFUs as the silylated reticulated open cell foam (ROCF Si) (6.45e6). This result is consistent with the silylated 30 phr chitosan foam having more free amino groups than the silylated reticulated open cell foam.

TABLE 1

| OPA Assay Results of 30 PHR Si with Reticulated Open Cell Foam ("ROCF") | | | |
|---|---|---|---|
| | 30 PHR Si | ROCF Si | OPA |
| | 13026850 | 6584950 | 1654498 |
| | 11297955 | 6021462 | 1685639 |
| | 13362349 | 6735590 | 1701811 |
| Mean | 12,562,385 | 6,447,334 | 1,680,649 |
| SEM | 1,107,803 | 376,428 | 24,048 |

Figure 5:
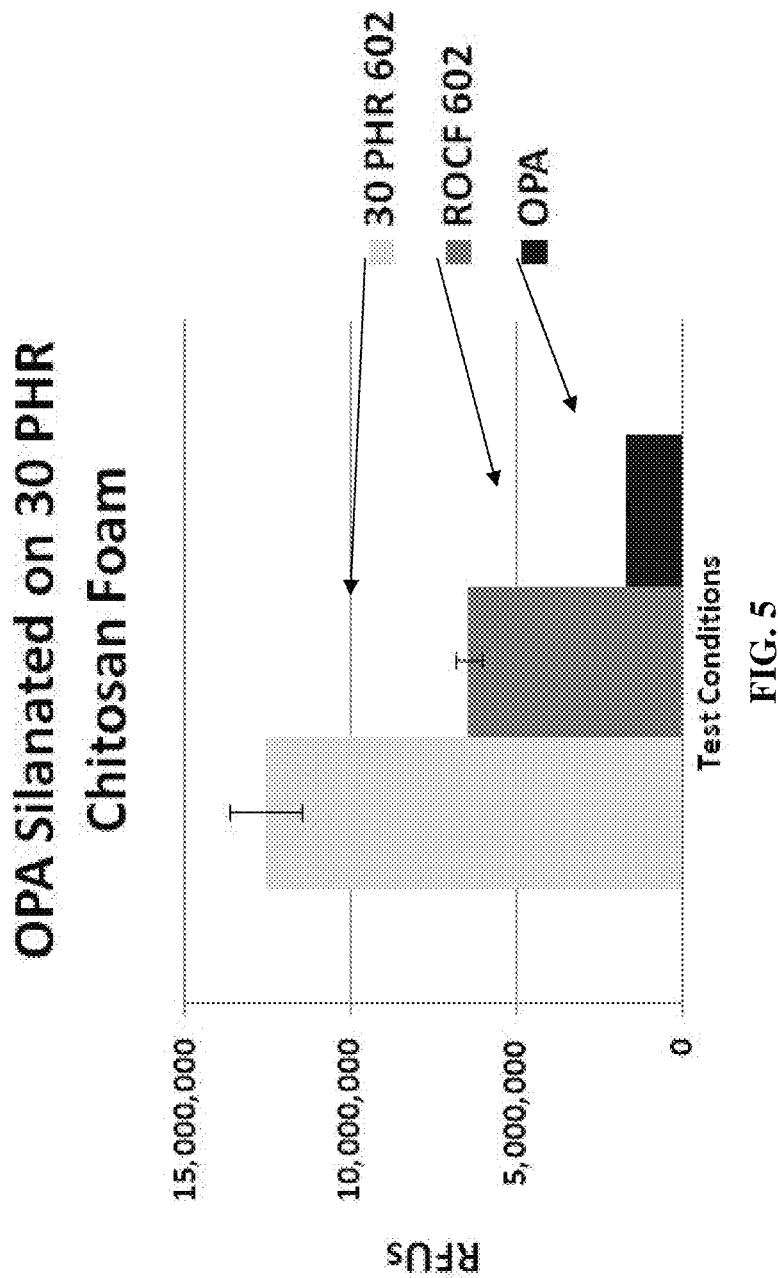
FIG. 5 depicts results comparing the number of free amino groups of silylated 30 phr chitosan foam ("30 PHR Si") with silylated reticulated open cell foam ("ROCF") using an o-phtaldialdehyde (OPA) assay. In both cases the silylation group was $(H_2N(CH_2)_3)(i-Pr)_2Si$— from the compound 602 (aminopropyldiisopropylethoxysilane). The results are provided in terms of relative fluorescence units (RFU). OPA alone, which is a sensitive detection reagent for amines, also serves as the control.

FIG. 5 depicts results comparing the number of free amino groups of silylated 30 phr chitosan foam ("30 PHR Si") with silylated reticulated open cell foam ("ROCF Si") using an o-phtaldialdehyde (OPA) assay. The results are provided in terms of relative fluorescence units (RFU). OPA alone, which is a sensitive detection reagent for amines, also serves as the control.

The equipment used in carrying out these experiments include:
Plate Reader (Biotek—Synergy 4)
TRITC capable microscope (Olympus—IX51)
A block of 30 phr chitosan foam
PBS Packs (Thermo Scientific 28384)
96-well, black, transparent bottom (Greiner 655209)
3-Aminopropyldiisopropylethoxysilane, Gelest Compound SIA0602.0 ("compound 602"). This compound was kept dessicated.
25 mL Glass ScintillationVials.
Ortho-pthaldialdehyde or OPA (Sigma P/N—P0532)
1 in cork boring tool
4 mm biopsy punch
The test procedure used included the following steps:
95% EtOH Solution was prepared.
15% 3-Aminopropyldiisopropylethoxysilane solution in 95% EtOH was prepared in a fume hood in a 25 mL scintillation vial and placed on shaker for 5 min.
PBS was prepared by mixing 1 pack PBS powder and 500 mL DI $H_2O$.
Sheets of 2 mm thick 30 phr foam were cut from a foam block using a deli slicer.
Coupons were punched out with a 1 inch cork boring tool.
All sample preparation steps were performed in glass scintillation vials.
Coupons were submerged in 10 mL vial of 15% silane solution and compressed against the bottom of the vial with a glass rod to remove any bubbles trapped inside the foam and placed on a shaker for 15 min. Negative controls were prepared by in a similar manner except that 10 mL of 95% EtOH solution was substituted for the silane solution.
The coupons were removed from the silane solution with forceps and transferred to a 95% EtOH bath and gently swirled approximately 3 seconds to wash off excess silane. This wash was then repeated.
The coupons were then transferred to a clean 250 mL beaker to ensure they are not touching each other.
The beaker was placed for 2 hours in an oven that was preheated to 80° C. After heating the beaker was removed from the oven and allowed it to cool at RT. Alternatively, you the coupons may be placed in beakers, uncovered, and allowed to incubate for 24 hr at RT.
Coupons were punched from the silylated and non-silylated 30 phr using a 4 mm biopsy punch. Each coupon was also weighed.
Quantification step:
200 µL of OPA was added to each coupon on a black 96-well plate, the plate covered and foil and incubated for 2 min at RT.
The plate was placed in the plate reader and the OPA Assay Protocol was initiated.

Example 2

Sulfo-EMCS Conjugation of a Capture Peptide to 30 PHR Chitosan Interfacial Layer A 30 per hundred resin (30 phr) chitosan prototype was formulated using 0.3 g of chitosan (Sigma P/N 448877) to 1.0 g polyurethane. The following test apparatuses, materials and procedures were used in carrying out these experiments.

The materials used in carrying out these experiments include:
1 in. silanated chitosan coupons.
Sulfo-EMCS (Pierce—22307)
BupH Borate Buffer Packs (Pierce—28372)
EDTA (Sigma Aldrich—E9885-500G)
25 mL Scintillation Vials.

The materials used in carrying out these experiments include:

The test procedure used included the steps listed below: All buffers and reagents were prepared in advance, except the Sulfo-EMCS, which was reconstituted immediately before use. See Sulfo-EMCS Product Instructions (Thermo Scientific-Pierce), which is incorporated by reference herein in its entirety.

1.1. BupH Borate Buffer: Two packs BupH Borate Buffer powderwere added to 1 L DI $H_2O$ as per manufacturer's instructions.

1.2. Conjugation Buffer, BupH Borate Buffer/5 mM EDTA was prepared by dissolving 146 mg EDTA in 500 mL BupH Borate Buffer.

1.3. Sulfo-EMCS, allowed to warm to RT, was reconstituted immediately before performing the Sulfo-EMCS addition step. 50 mg Sulfo-EMCS was reconstituted in 1.22 mL BupH Borate Buffer/EDTA for a 100× stock per manufacturer's instructions.

1.4. Capture peptides were reconstituted according to manufacturer's instructions. A 10 mM working solution was prepared.

| | |
|---|---|
| Peptide Stock Solution: Peptide 22 | |
| mol of peptide/volume diluent = final conc | |
| peptide | |
| concentration: | 10 mM |
| Reaction mixture: | |
| Peptide: | |
| Dissolve Peptide in H2O. | |
| Desired Concentration Per | |
| Reaction: | 150 uM |
| Sulfo-EMCS: | |
| Reconstitute 41 mg ECMS in 1.22 mL BupH PBS for a 100 mM stock. | |
| Add EMCS to reaction mixture based on the # moles desired | |

1.5. Sample preparation steps were performed in glass scintillation vials to minimize the amount of protein and peptide adsorbed by the vial.

1.6. Overview. The experiment proceeded as follows (~2.5 hr): Reaction Mixture 1→Wash→Reaction Mixture 2→Wash→Used or stored at 4° C.

1.7.

| Reaction Mixture 1: | 100× Sulfo-EMCS |
|---|---|
| EMCS | |
| BupH Borate Buffer/EDTA | 5.100E−03 |
| Reaction Mixture 2: | Peptide |
| Peptide | |
| BupH Borate Buffer/EDTA | |

1.8. Reaction Mixture 1: 100× Sulfo-EMCS preparation. This reaction bound the Sulfo-EMCS to the modified chitosan substrate.

1.8.1. Preparation of Sulfo-EMCS. Add 1.22 mL of BupH Borate Buffer/EDTA was added to a 50 mg vial of Sulfo-EMCS and then shaken well and vortexed for ~10 sec. Then it was allowed to dissolve for ~2 min, and it was used within 15 minutes of reconstituting.

1.8.2. Transfer chitosan coupons from Example 1 to each vial of reaction mixture. The negative control has no Sulfo-EMCS or peptide; BupH Borate Buffer/EDTA was substituted for these reagents in the reaction.

1.8.3. A glass rod was used to compress the silanated chitosan coupons to ensure even reactivity with the foam surfaces.

1.8.4. The reaction 1 mixture was placed in a shaker at RT for 30 min.

1.9. Once the Sulfo-EMCS was conjugated, the coupons were washed in BupH Borate Buffer. A glass rod was used to squeeze the bubbles out of the coupons to ensure all excess Sulfo-EMCS is removed.

1.10. Preparation of Reaction Mixture 2: Peptide Reaction.

1.10.1. The EMCS-bound foam was added to the capture peptide (P22, a commercially available anti-GM-CSF Peptide) and BupH Borate Buffer/EDTA mix into each reaction vial.

1.10.2. A glass rod was used to compress the foam coupons to ensure even reactivity with the foam surfaces.

1.10.3. Reaction Mixture 2 was placed on a shaker at RT for 30 min. This conjugated the capture peptide to the Sulfo-EMCS crosslinker deposited on the foam.

1.11. The coupons were then washed in BupH Borate Buffer to remove excess peptide. Again, use a clean glass rod to remove the bubbles to ensure even washing.

1.12. Use the coupons immediately for growth factor binding or transfer the moist coupons to a capped vial and store them at 4° C. until ready for use for no longer than. 7-10 days.

Figure 8:
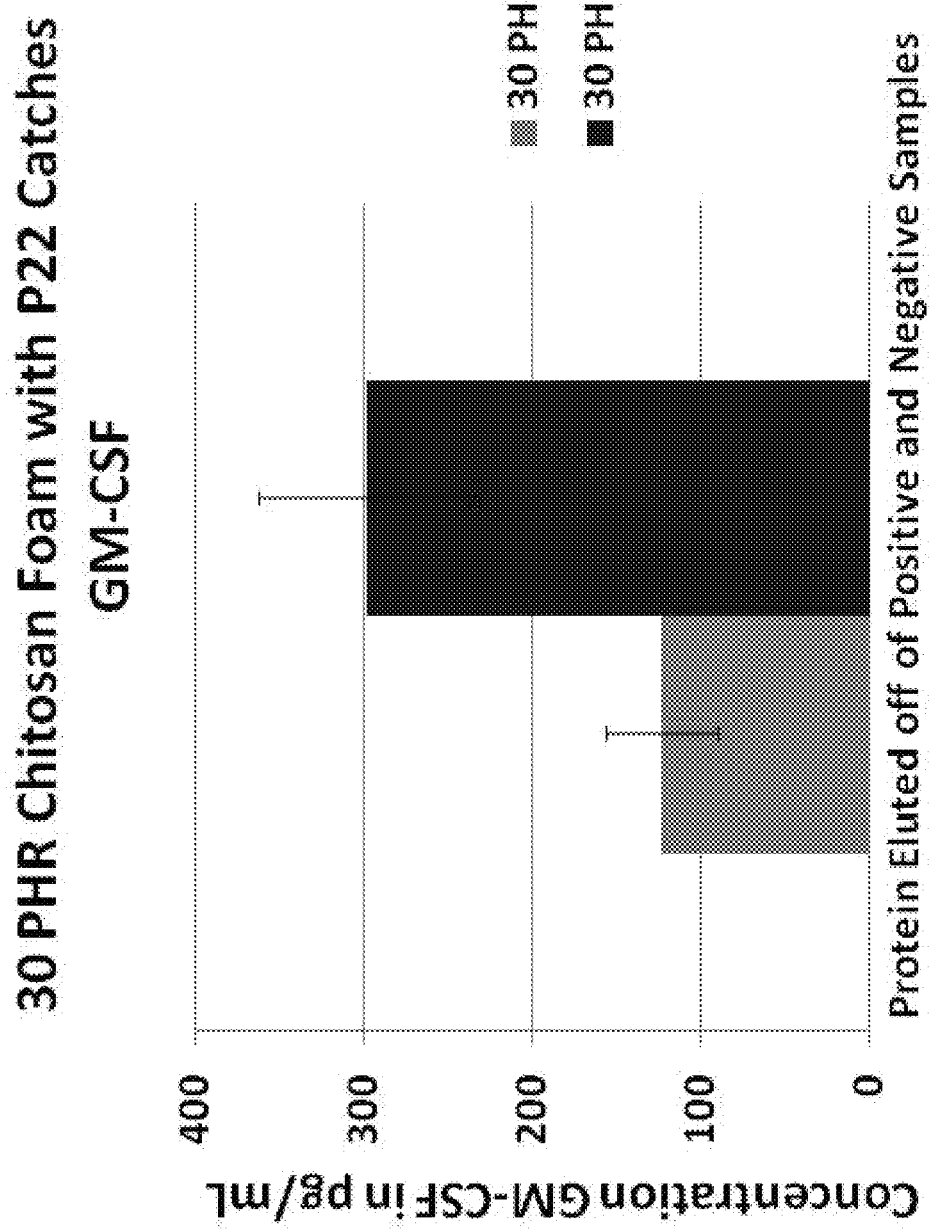
FIG. 8: Silylated with compound 602, 30 PHR Chitosan/ P-22 captures more granulocyte macrophage colony stimulating factor (GM-CSF). Briefly, 333 ng/mL of GM-CSF was incubated with the samples for 24 hr. The unbound protein was washed off then the samples were eluted with an imidazole-based buffer, E1. The samples were cleaned up via buffer exchange with PBS and quantified by ELISA. The results indicate that the positive sample with P-22 captured 299 pg/mL of GM-CSF, whereas the 30 PHR alone bound 124 pg/mL.
Figure 10:
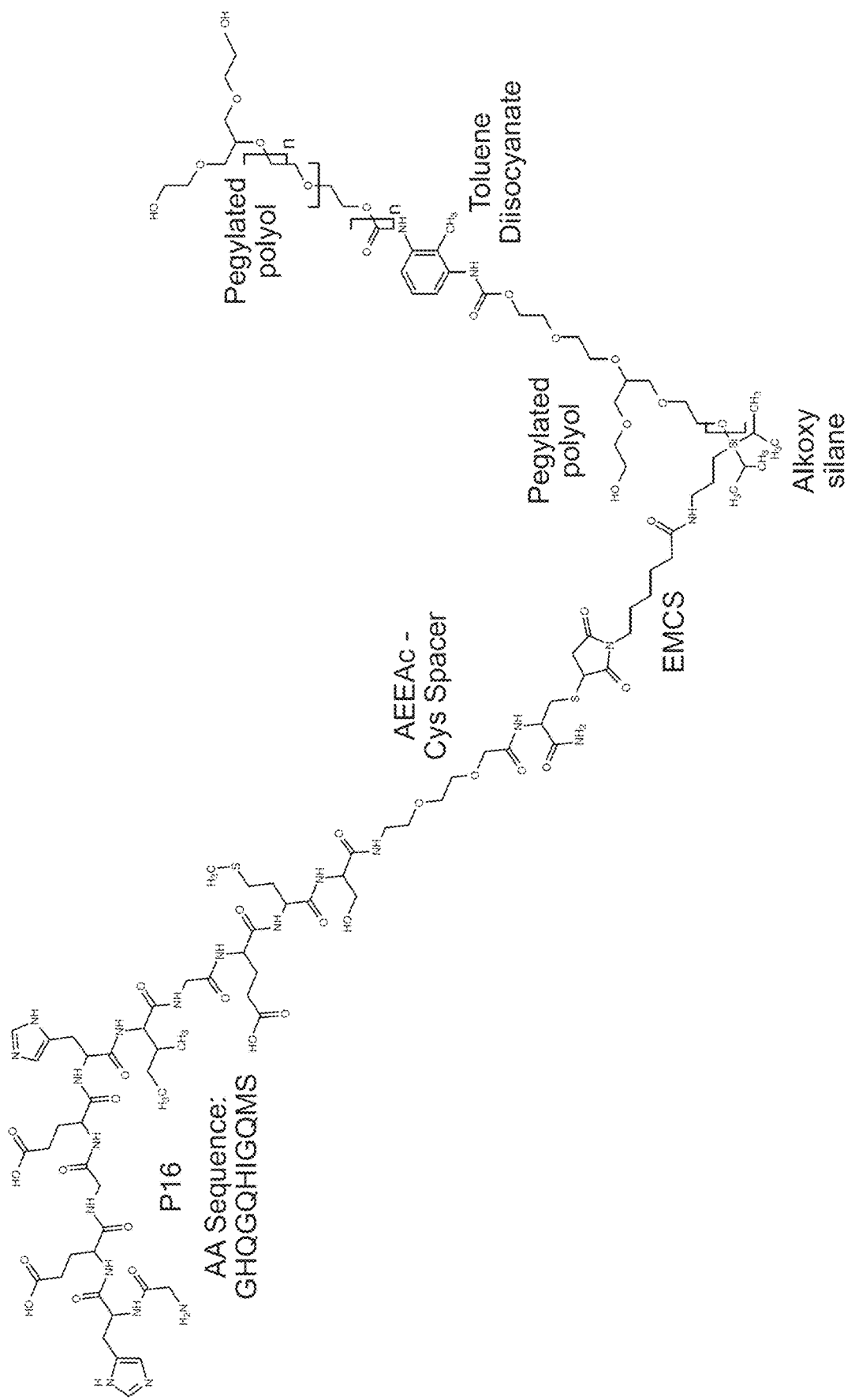
FIG. 10 provides structure and connectivity information for a portion of an aptamer-modified polymeric foam embodiment comprising an oligopeptide (P16; SEQ ID NO: 2), an AEEAc-Cys linker, an EMCS linker, a substituted silyl group, and a polyurethane backbone based on a PEGylated triol and a toluene diisocyanate.

1.13. 333 ng/mL of granulocyte macrophage colony stimulating factor (GM-CSF) GM-CSF was incubated with the samples for 24 hr. The unbound proteins were washed off then the samples were eluted with an imidazole-based buffer, E1 before a buffer exchange with PBS and quantification via ELISA. The results indicate that the positive sample with P-22 captured 299 pg/mL of GM-CSF, whereas the negative sample bound 124 pg/mL. See FIG. 8.

Example 3

P22 Modified Open Cell Reticulated Polymer and Capture of CM-CSF

In this study ROCF was substituted for the chitosan substrate described in the examples above. DyLight® Fluor Texas Red® (Thermo Scientific P/N 46412) was used instead of OPA. It is an $NH_2$-reactive dye as well; however, it fluoresces at a different wavelength.

Gelest Compound 630 was used instead of Gelest Compound SIA0602.0. Compound 630 has a shorter alkane chain and no propyl groups but carries out the same basic function.

Figure 6:
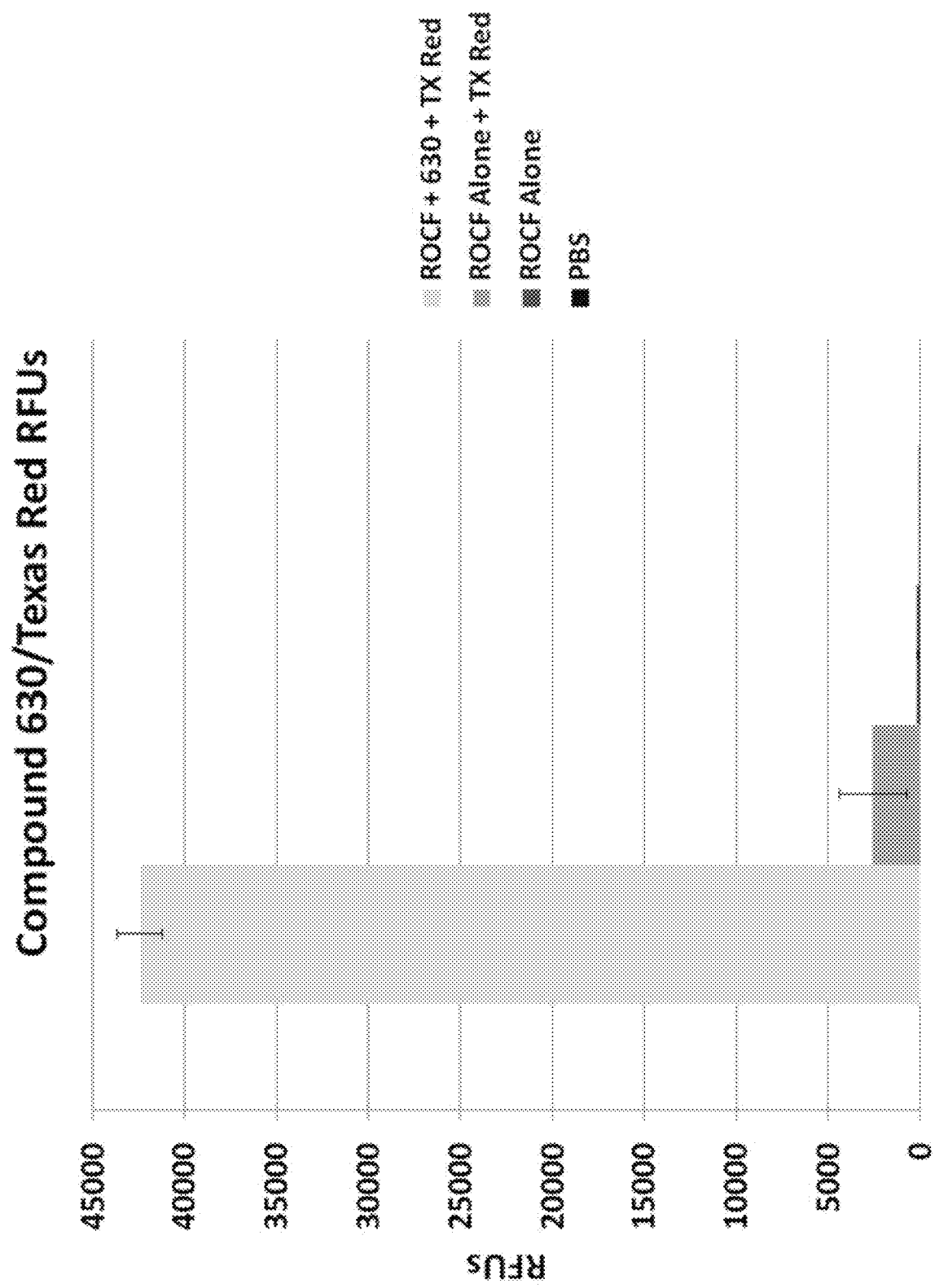
FIG. 6 depicts results comparing the relative fluorescence units ("RFUs") of reticulated open cell foam that was silylated with the group $(H_2N(CH_2)_{11})(EtO)_2Si$— from compound 630 (aminoundecyltriethoxysilane) and treated with Texas Red® with non-silylated reticulated open cell foam ("ROCF"), alone and together with Texas Red®. The results are provided in terms of relative fluorescence units (RFU). PBS, and ROCF in PBS were also analyzed to ensure that autofluorescence of these materials would not skew RFU readings. PBS is phosphate buffered saline.

Fluorometric Analysis of -Sil bound to ROCF. In order to determine the amount of silyl or substituted silyl groups bound to the ROCF, Texas Red® fluorescent dye, an $NH_2$-reactive fluorophore, was conjugated to the 630 linker for visualization and quantification. 630's heterobifunctionality enables its Si atom at one end to bind to —OH groups on the foam while the other end presents a —NH₂ group that facilitates NH₂-reactive chemistries. Once the 630 was deposited onto the ROCF, incubation with Texas Red® identified the presence of the crosslinkers on the ROCF. Fluorescent analysis showed successful deposition of silyl or substituted silyl groups compound 630 to ROCF (FIGS. 9A & 9B). Fluorometric quantification of the test group indicated approximately 42,000 RFUs at an Ex/Em of 584/630, whereas the negative control, ROCF without the silyl or substituted silyl groups yielded a total of 2,586.5 RFUs due to background levels of ROCF/dye interaction (FIG. 6). Therefore, -Sil conjugation resulted in a ~16-fold increase in fluorescence, which corresponds to the number of -Sil linkers deposited on the foam. PBS, and ROCF in PBS were also analyzed to ensure that autofluorescence of these materials would not skew RFU readings. Data are given as mean±standard deviation.

Figure 11:
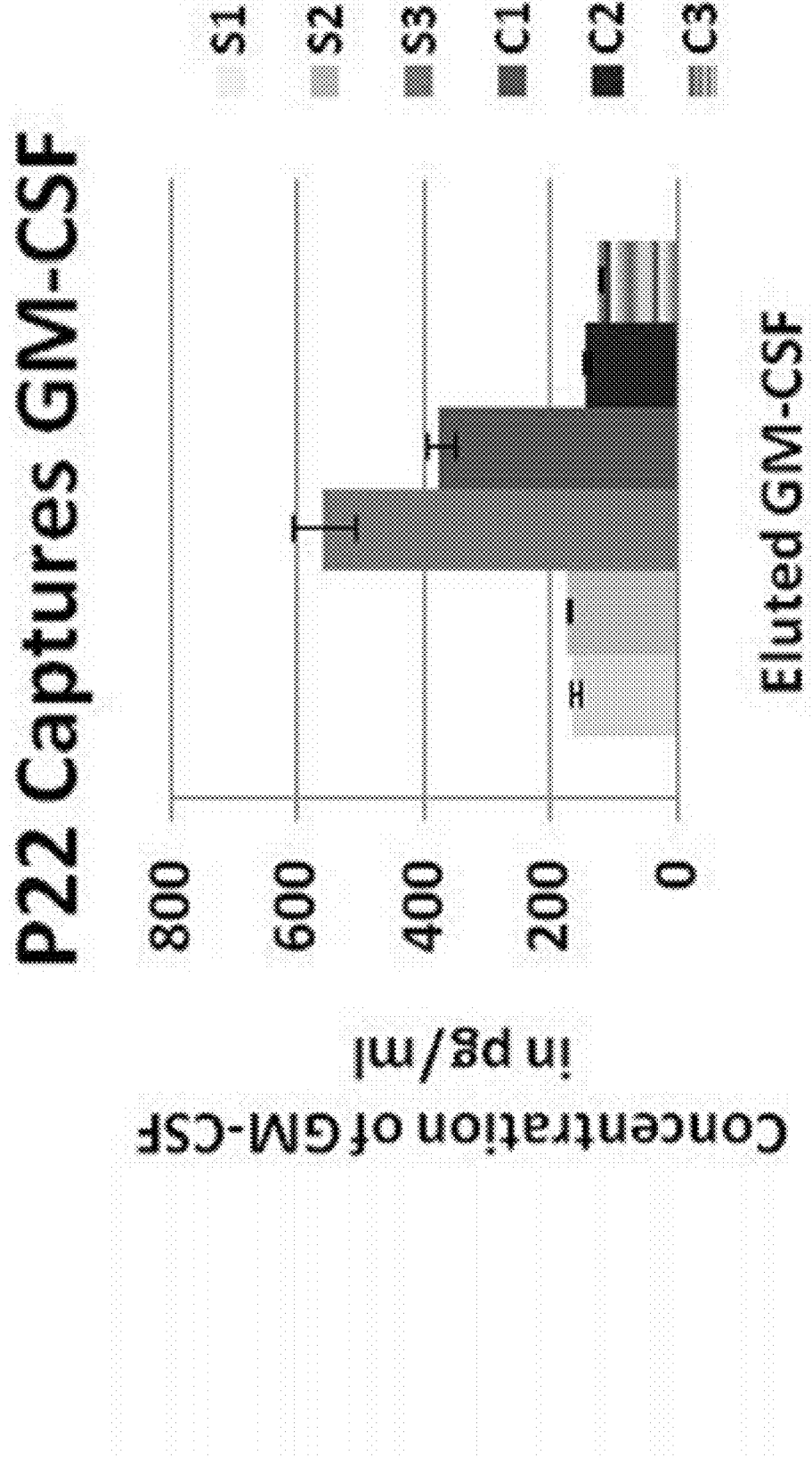
FIG. 11 provides elution results for the P22/GM-CSF experiment. P22 was obtained from the Bachem Americas Inc. 2010 peptide catalog. P22 is a GM-CSF antagonist that binds GM-CSF in an inhibitory manner. Briefly, 330 nmol P22 was conjugated to a polyurethane-based ROCF via Sulfo-EMCS chemistry. The P22-linker-foam construct was incubated with 1 µg GM-CSF overnight, washed five times, and subjected to stringent elutions. The wash preceding the elutions showed that non-specifically bound protein was reduced to negligible levels (<100 pg/mL). Upon elution, the sample with the most capture peptide, S3, outperformed ROCF alone by 49%. The total amount of GM-CSF bound to ROCF/P22, 608 pg/mL, was greater than the amount of GM-CSF bound non-specifically to the negative control, C1, 376 pg/mL. Samples S1-S3 all contained peptide-linker-foam with Sulfo-EMCS concentration increasing from 51 to S3 (51=10× Sulfo-EMCS+P22; S2=25× Sulfo-EMCS+P22 and S3=50× Sulfo-EMCS+P22), C1 was ROCF alone, C2 was Silanated ROCF+EMCS–P22 and C3 was Silanated ROCF–EMCS+P22. There were no positive controls available for this experiment, as no technology has yet been proven to covalently conjugate peptides to polyurethane. However, positive controls were later developed for subsequent experiments based on experimental results. Data are given as mean±standard deviation.
Figure 12:
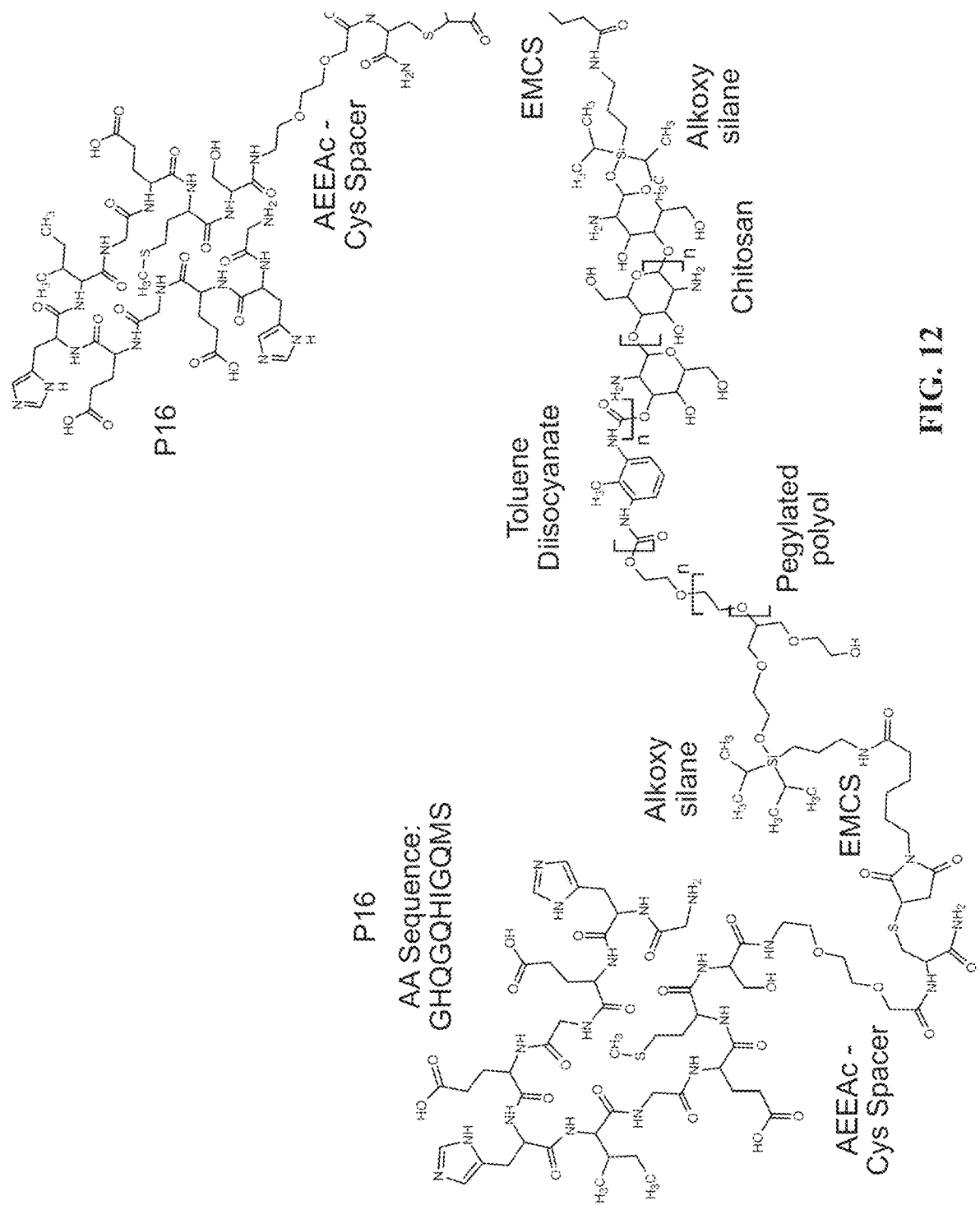
FIG. 12 provides structure and connectivity information for a portion of an aptamer-modified polymeric foam embodiment comprising an oligopeptide (P16; SEQ ID NO: 2), an AEEAc-Cys linker, an EMCS linker, a substituted silyl group, and a polyurethane-copolymer based on a PEGylated triol, a toluene diisocyanate and a chitosan oligomer.
Figure 13:
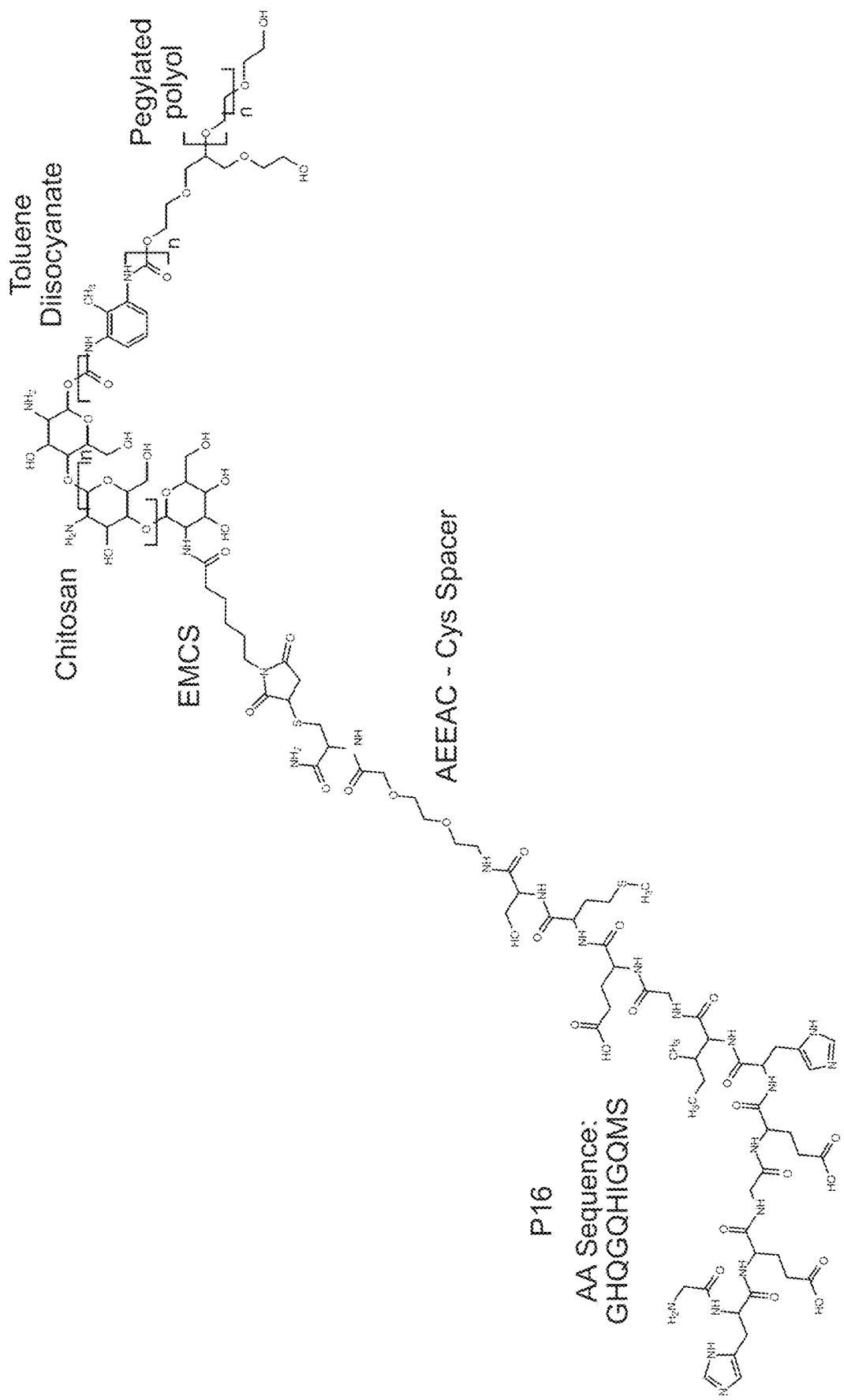
FIG. 13 provides structure and connectivity information for a portion of an aptamer-modified polymeric foam embodiment comprising an oligopeptide (P16; SEQ ID NO: 2), an AEEAc-Cys linker, an EMCS linker, and a polyurethane-copolymer based on a PEGylated triol, a toluene diisocyanate and a chitosan oligomer.

With the -Sil bond, a "capture peptide" was next conjugated to the amino-functionalized ROCF. To do so, Sulfo-EMCS chemistry developed in Example 2 was used to conjugate a commercially available GM-CSF antagonist capture peptide, P22, to ROCF. The P22-linker-foam construct was incubated with GM-CSF, washed stringently and eluted. The eluted GM-CSF was quantified via ELISA (FIG. 11). The sample with the most P22, S3, captured 49% more GM-CSF than ROCF alone. The total amount of GM-CSF captured by ROCF/P22, 608 pg/mL, was greater than the amount of GM-CSF bound non-specifically to the negative control, ROCF alone, 376 pg/mL. Samples S1-S3 all consisted of P22-linker-foam with Sulfo-EMCS concentration increasing from S1 to S3.

Elution results for the P22/GM-CSF experiment: P22 was obtained from the Bachem Americas Inc. 2010 peptide catalog. P22 is a GM-CSF antagonist that binds GM-CSF in an inhibitory manner. Briefly, 330 nmol P22 was conjugated to ROCF via Sulfo-EMCS chemistry. The P22-linker-foam construct was incubated with 1 µg GM-CSF overnight, washed five times, and subjected to stringent elutions. The wash preceding the elutions showed that non-specifically bound protein was reduced to negligible levels (<100 pg/mL). Upon elution, the sample with the most capture peptide, S3, outperformed ROCF alone by 49%. The total amount of GM-CSF bound to ROCF/P22, 608 pg/mL, was greater than the amount of GM-CSF bound non-specifically to the negative control, Cl, 376 pg/mL. Samples S1-S3 all consisted of peptide-linker-foam with Sulfo-EMCS concentration increasing from S1 to S3. There were no positive controls available for this experiment, as no technology has yet been proven to covalently conjugate peptides to polyurethane. However, positive controls were later developed for subsequent experiments based on experimental results. Data are given as mean ±standard error.

Example 4

P16 Modified Polymers and Capture of VEGF

P16, an anti-VEGF peptide, was designed de novo. The design was based on the dimeric X-ray crystallography structure of the VEGF dimer. The amino acid residues in the true biological design can be modified to enhance or reduce binding affinities.

P16 was designed de novo. P16 was based on the X-ray crystallography structure of the VEGF dimer, registered as accession number 1vpf in the Protein Data Bank. The P16 peptide design mimics the natural phenomenon of dimerization that takes place between two VEGF homodimers.

P16 consists of an 11 aa sequence that mimics the dimeric interface of Chain C in Protein Data Bank structure 1vpf. The P16 sequence consists mostly of hydrophobic residues with a few charged residues scattered throughout. The sole substitution is at aa1, where we substituted a glycine for a proline to minimize steric interference from the proline.

Figure 14:
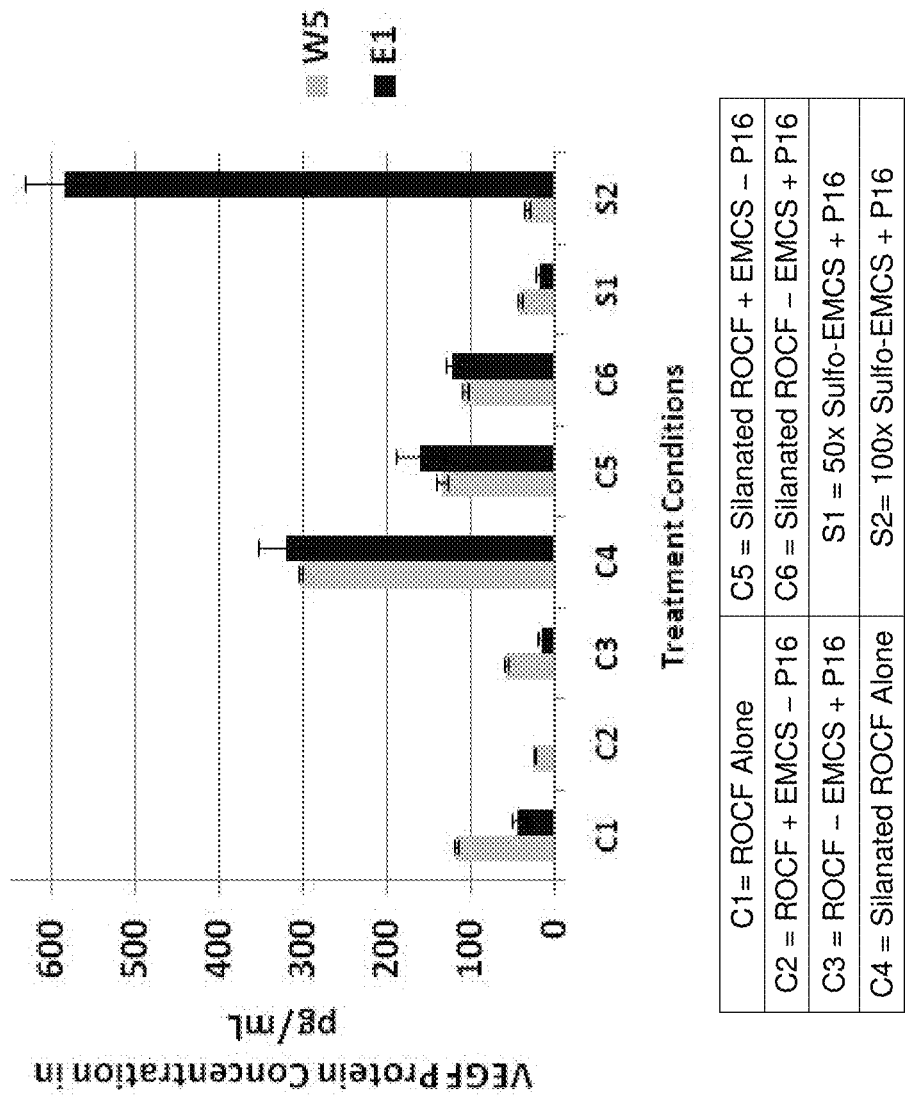
FIG. 14 shows that ROCF captures 82% more VEGF with P16 (a de novo designed capture peptide for VEGF) covalently bound to it. C1 was ROCF alone; C2 was ROCF+ EMCS–P16; C3 was ROCF–EMCS+P16; C4 was silanated ROCF alone; C5=silanated ROCF+EMCS–P16; C6 was silanated ROCF–EMCS+P16; S1 was 50× Sulfo-EMCS+ P16; and S2 was 100× Sulfo-EMCS+P16. W=Final subsequent PBS wash. E1=50 mM Tris, 80 mM NaCl, 250 mM Imidazole, 45 min. W5 (left) shows VEGF (pg/mL) non-specifically retained in the ROCF in the final PBS wash. E1 (right) indicates the amount of VEGF dislodged from the foam and peptide with an organic solvent after the last wash. The elution data indicate that S2 (P16-linker-foam) bound 82% more VEGF than C4 (silanated ROCF), the negative control with the most abundant bound VEGF. S2 bound 584 pg/mL, whereas C4 bound 321 pg/m. S2 has the highest concentration of EMCS and therefore the most covalently bound P16. This data shows the strong correlation between the amount of P16 covalently linked to the foam and the amount of target protein caught by the foam. Data are given as mean±standard deviation.

Further experiments demonstrate that P16 captures the protein target VEGF. ELISA results from P16/VEGF experiments indicated that P16 captured its protein target, VEGF (FIG. 14). P16 was conjugated to ROCF, incubated with VEGF, washed stringently, then eluted with an organic solvent. In this experiment, the test group (P16-linker-foam) bound 584 pg/mL, whereas the greatest negative control bound 321 pg/mL. Non-specific binding was expected due to the hydrophobic nature of both the ROCF and the target protein VEGF. However, these data indicate that structure-based peptide design enhanced target-specific protein capture beyond the non-specific hydrophobic properties of the ROCF.

The results summarized in both Examples 3 & 4 show that -Sil groups were successfully conjugated to ROCF. Fluorometric quantification of the positive test group indicated 21,702.5 RFUs at an Ex/Em of 584/630, whereas the negative control, ROCF without -Sil, yielded a total of 2,586.5 RFUs due to background levels of ROCF/dye interaction. P16 and P22 were successfully conjugated to the linkers deposited on the ROCF substrate. Finally, it was possible to quantify the effectiveness of P16 and P22 capturing their target proteins. In the case of P16, the elution data indicate that the positive sample bound 82% more VEGF than the greatest negative control, silanated ROCF. The positive sample bound 584 pg/mL, whereas the negative sample bound 321 pg/mL. For P22, the sample with the most capture peptide outperformed ROCF alone by 49%. The total amount of GM-CSF bound to ROCF/P22, 608 pg/mL, was greater than the amount of GM-CSF bound non-specifically to the negative control, 376 pg/mL.

We claim:

1. A wound dressing comprising a polymer foam substrate conjugated to a polypeptide, wherein the polypeptide comprises a sequence at least 90% identical to SEQ ID NO:1 or a sequence at least 90% identical to SEQ ID NO: 2.

2. The wound dressing of claim 1, wherein the polypeptide is covalently attached to the polymer foam.

3. The wound dressing of claim 1, wherein the polypeptide is attached via one or more linkers.

4. The wound dressing of claim 3, wherein the polypeptide is attached to the polymer foam through a thioether linkage.

5. The wound dressing of claim 1, wherein the amino or carboxyl terminus of the polypeptide comprises a polyethylene glycol (PEG) spacer-cysteine residue.

6. The wound dressing of claim 3, wherein the linker is an N-(e-maleimidocaproyloxy) sulfosuccinimide ester-derived linker (EMCS-derived linker) or a sulfo-EMCS-derived linker.

7. The wound dressing of claim 6, wherein the polymer foam comprises a substituted silyl derived linker.

8. The wound dressing of claim 7, wherein the substituted silyl derived linker is derived from aminoundecyltriethoxysilane or aminopropyldiisopropylethoxysilane.

9. The wound dressing according to claim 1, further comprising a growth factor, chemokine or cytokine bound to the wound dressing.

10. A wound dressing comprising a polyurethane foam substrate, wherein the polyurethane foam substrate comprises a co-polymer, and wherein the co-polymer comprises a repeat unit formed by polymerization of a pre-polymer and an aminoglycoside, and further comprising an aptamer covalently attached directly or via one or more linkers to the repeat unit of the co-polymer; wherein the pre-polymer comprises an isocyanate and the aminoglycoside is selected from the groups consisting of chitosan, glucosamine, neomycin, dibekacin, kanamycin, tobramycin, streptomycin, and gentamicin.

11. The wound dressing of claim 10, wherein the polyurethane foam substrate is a reticulated open-celled foam.

12. The wound dressing of claim 10, wherein the aptamer is attached to the polymer foam substrate via one or more linkers.

13. The wound dressing of claim 12, wherein the aptamer is covalently attached to the one or more linkers through a thioether linkage.

14. The wound dressing of claim 12, wherein the linker is an N-(e-maleimidocaproyloxy) sulfosuccinimide ester-derived linker (EMCS-derived linker) or a sulfo-EMCS-derived linker.

15. The wound dressing of claim 12, wherein the linker is a substituted silyl-derived linker.

16. The wound dressing of claim 15, wherein the substituted silyl-derived linker is derived from aminoundecyltriethoxysilane or aminopropyldiisopropylethoxysilane.

17. A method for treating a wound comprising contacting a wound site with a wound dressing of claim 1.

18. A method for treating a wound comprising contacting a wound site with a wound dressing of claim 10.

* * * * *

UNITED STATES PATENT AND TRADEMARK OFFICE
CERTIFICATE OF CORRECTION

Page 1 of 3

PATENT NO. : 10,624,984 B2
APPLICATION NO. : 15/172552
DATED : April 21, 2020
INVENTOR(S) : James Courage It is certified that error appears in the above-identified patent and that said Letters Patent is hereby corrected as shown below:

On the Title Page

<u>Item [56], Page 3, Column 2</u>
Line 10, delete "Hypermia" and insert -- Hyperemia --, therefor.

In the Specification

<u>Column 2</u>
Lines 4-8, delete "In some embodiments, aptamer is an the oligopeptide having 8 to 12 residues. In some embodiments, the oligopeptide has the sequence GHQGQHIGQMS (SEQ ID NO: 2). In some embodiments, aptamer is P16. In some embodiments, aptamer is P22." and insert the following paragraph:
-- In certain embodiments a wound dressing is provided comprising a polymer foam substrate conjugated to a polypeptide, wherein the polypeptide comprises an amino acid sequence identical to SEQ ID NO: 1 (P22; AIQEARRLLNLSRD), a sequence at least 90% identical to SEQ ID NO:1 or a sequence comprising 1, 2, or 3 amino acid substitutions or deletions relative to SEQ ID NO: 1. In some aspects, the amino acid sequence further comprises an amino or carboxyl terminal Cys residue (e.g., the amino or carboxyl terminus of a polypeptide of the embodiments comprises a PEG spacer-cysteine residue). For example, the amino acid sequence can comprise the sequence AEEAc-Cys-NH2 (SEQ ID NO: 3) at the C-terminus. --, therefor.

<u>Column 3</u>
Line 43, delete "o-phtaldialdehyde" and insert -- o-phthaldialdehyde --, therefor.

<u>Column 4</u>
Line 32, delete "51" and insert -- S1 --, therefor.

Signed and Sealed this
Thirty-first Day of August, 2021

Drew Hirshfeld
*Performing the Functions and Duties of the
Under Secretary of Commerce for Intellectual Property and
Director of the United States Patent and Trademark Office*

Line 33, delete "(51" and insert -- (S1 --, therefor.

Column 5
Line 57, delete "a a" and insert -- a --, therefor.

Column 8
Line 44, delete "alkanediyl$_{(C\leq 6)}$;" and insert -- alkanediyl$_{(C\leq 20)}$; --, therefor.
Line 62, delete "STAB," and insert -- SIAB, --, therefor.

Column 9
Line 61, after "is" delete "an".
Line 63, delete "GHQGQHIGQMS." and insert -- GHQGQHIGQMS (SEQ ID NO: 2). --, therefor.

Column 10
Line 13, delete "arenediyl$_{(\leq 6)}$;" and insert -- arenediyl$_{(\leq 6)}$-; --, therefor.

Column 15
Line 50, delete ""alkenediyl"" and insert -- "alkanediyl" --, therefor.
Line 65, delete ""alkenediyl"" and insert -- "alkanediyl" --, therefor.

Column 19
Line 21, delete "simple monosachharides" and insert -- Simple monosaccharides --, therefor.
Line 63, delete "t-" and insert -- α- --, therefor.

Column 25
Line 37, delete "trisiocyanate" and insert -- triisocyanate --, therefor.

Column 27
Line 37, delete "linke$_1$" and insert -- linker$_1$ --, therefor.
Line 42, delete "linke$_1$" and insert -- linker$_1$ --, therefor.

Column 28
Line 12, delete "NH$_2$," and insert -- NH$_2$ (SEQ ID NO: 2-AEEAc-Cys-NH$_2$), --, therefor.

Column 37
Line 62, delete "poloymers" and insert -- polymers --, therefor.

Column 38
Line 59, delete "cytoxicity)." and insert -- cytotoxicity). --, therefor.

Column 39
Line 23, delete "Silanation" and insert -- Silanization --, therefor.
Line 37, delete "o-phtaldialdehyde" and insert -- o-phthalaldehyde --, therefor.
Line 64, delete "o-phtaldialdehyde" and insert -- o-phthalaldehyde --, therefor.

Column 40
Line 11, delete "dessicated." and insert -- desiccated. --, therefor.

In the Claims

Column 45
Lines 52-53, Claim 1, delete "comprises" and insert -- consists of --, therefor.

Column 46
Line 52, Claim 7, delete "claim 6," and insert -- claim 3, --, therefor.

Column 47
Line 2, Claim 10, delete "groups" and insert -- group --, therefor.